(12) United States Patent
Warren

(10) Patent No.: US 12,569,639 B2
(45) Date of Patent: **\*Mar. 10, 2026**

(54) EFFICIENT ENRICHED OXYGEN AIRFLOW SYSTEMS AND METHODS

(71) Applicant: WEARAIR VENTURES, INC., Medicine Hat (CA)

(72) Inventor: John Warren, Melville (CA)

( \* ) Notice: Subject to any disclaimer, the term of this patent is extended or adjusted under 35 U.S.C. 154(b) by 801 days.

This patent is subject to a terminal disclaimer.

(21) Appl. No.: 17/870,820

(22) Filed: Jul. 21, 2022

(65) Prior Publication Data

US 2023/0023722 A1 Jan. 26, 2023

Related U.S. Application Data

(63) Continuation-in-part of application No. 17/850,804, filed on Jun. 27, 2022, now Pat. No. 11,951,260, (Continued)

(51) Int. Cl.
| | |
|---|---|
| *A61M 16/10* | (2006.01) |
| *A61M 16/00* | (2006.01) |
| *A61M 16/06* | (2006.01) |

(52) U.S. Cl.
CPC ........ *A61M 16/101* (2014.02); *A61M 16/024* (2017.08); *A61M 16/0672* (2014.02);
(Continued)

(58) Field of Classification Search
CPC ............ A61M 16/101; A61M 16/0672; A61M 16/024; A61M 2016/0036;
(Continued)

(56) References Cited

U.S. PATENT DOCUMENTS

| | | | |
|---|---|---|---|
| 3,533,221 | A | 10/1970 | Tamura |
| 4,971,609 | A | 11/1990 | Pawlos |

(Continued)

FOREIGN PATENT DOCUMENTS

| | | |
|---|---|---|
| CA | 2810669 | 3/2012 |
| CN | 202322372 | 7/2012 |

(Continued)

OTHER PUBLICATIONS

Final Office Action on Aug. 2, 2023 for U.S. Appl. No. 17/850,804.
(Continued)

*Primary Examiner* — Paige Kathleen Bugg
(74) *Attorney, Agent, or Firm* — Transformative Legal LLC; Len S. Smith; Julie E. Kurzrok

(57) ABSTRACT

The present invention provides new devices, systems, and methods for delivering enriched oxygen to recipients (e.g., chronically ill patients, such as COPD patients). One aspect is a more efficient portable oxygen concentrator that is configured to deliver an enriched oxygen airflow having a significantly lower overall oxygen concentration and greater overall volume administered as compared to currently marketed or known portable oxygen concentrators. Administering the lower oxygen concentration at higher volumes allows for the present portable oxygen concentrators to deliver an equivalent number of moles of oxygen as administered by traditional portable concentrators while increasing the efficiency of the system and the ability of the system to maintain the therapeutic level of oxygen concentration for a longer period.

13 Claims, 5 Drawing Sheets

Related U.S. Application Data which is a continuation of application No. 17/141,085, filed on Jan. 4, 2021, now abandoned.

(60) Provisional application No. 62/995,224, filed on Jan. 21, 2020.

(52) U.S. Cl.
CPC ............... *A61M 2016/0036* (2013.01); *A61M 2016/1025* (2013.01); *A61M 2202/0057* (2013.01); *A61M 2202/0208* (2013.01); *A61M 2202/0266* (2013.01); *A61M 2205/3334* (2013.01)

(58) Field of Classification Search
CPC .. A61M 2016/1025; A61M 2202/0057; A61M 2202/0208; A61M 2202/0266; A61M 2205/3334
USPC ...................................................... 128/205.12
See application file for complete search history.

(56) References Cited

U.S. PATENT DOCUMENTS

| | | | | |
|---|---|---|---|---|
| 6,520,176 | B1 | 2/2003 | Dubois | |
| 6,651,658 | B1 | 11/2003 | Hill | |
| 6,691,702 | B2 | 2/2004 | Appel | |
| 7,763,103 | B2 | 7/2010 | Dolensky | |
| 8,894,751 | B2 | 11/2014 | Galbraith | |
| 9,717,876 | B2 | 8/2017 | Wilkinson | |
| 9,974,918 | B2 | 5/2018 | Armstrong | |
| 9,974,919 | B2 | 5/2018 | Richard | |
| 10,583,265 | B2 | 3/2020 | Whitcher | |
| 10,799,663 | B1 | 10/2020 | Oddo | |
| 11,951,260 | B2* | 4/2024 | Warren | A61M 16/024 |
| 2003/0167924 | A1* | 9/2003 | McCombs | B01D 53/053 96/111 |
| 2006/0185668 | A1* | 8/2006 | Jagger | A61M 16/101 128/203.26 |
| 2006/0230931 | A1 | 10/2006 | Bliss | |
| 2007/0227360 | A1* | 10/2007 | Atlas | A61M 16/101 96/121 |
| 2009/0320845 | A1* | 12/2009 | Fishman | A61P 25/00 514/250 |
| 2010/0116270 | A1 | 5/2010 | Edwards | |
| 2011/0197890 | A1 | 8/2011 | Jagger | |
| 2011/0232483 | A1* | 9/2011 | Haberland | A61M 16/0672 96/110 |
| 2011/0247620 | A1* | 10/2011 | Armstrong | A61M 16/0677 128/207.18 |
| 2012/0000462 | A1 | 1/2012 | Edwards | |
| 2012/0266883 | A1 | 10/2012 | Taylor | |
| 2014/0345609 | A1 | 11/2014 | Whitcher | |
| 2015/0059764 | A1 | 3/2015 | Metelits | |
| 2015/0083121 | A1 | 3/2015 | Fisher | |
| 2020/0179638 | A1* | 6/2020 | Oddo | B01D 53/047 |
| 2020/0306486 | A1 | 10/2020 | Oddo | |
| 2020/0360644 | A1 | 11/2020 | Westfall | |
| 2021/0093824 | A1 | 4/2021 | Colefax | |
| 2021/0113801 | A1* | 4/2021 | Wang | A61M 16/105 |
| 2021/0154427 | A1* | 5/2021 | Poon | B01D 53/261 |
| 2021/0196916 | A1 | 7/2021 | Rauker | |
| 2023/0023722 | A1 | 1/2023 | Warren | |

FOREIGN PATENT DOCUMENTS

| | | |
|---|---|---|
| EP | 1401557 | 3/2004 |
| EP | 1637209 | 3/2006 |
| EP | 3193996 | 7/2017 |
| GB | 955894 | 4/1964 |
| JP | 2007536759 | 5/2008 |
| JP | 2008517638 | 5/2008 |
| JP | 2010227517 | 10/2010 |
| WO | WO2011127314 | 10/2011 |
| WO | WO2015015852 | 2/2015 |
| WO | WO2019202390 | 10/2019 |
| WO | WO2020037375 | 2/2020 |

OTHER PUBLICATIONS

Non-Final Office Action on Apr. 30, 2021 for U.S. Appl. No. 17/141,085.
Final Office Action on Aug. 17, 2021 for U.S. Appl. No. 17/141,085.
Non-Final Office Action on Dec. 27, 2021 for U.S. Appl. No. 17/141,085.
Non-Final Office Action on Mar. 1, 2023 for U.S. Appl. No. 17/850,804.
Sakaue, et al., "Oxygen Inhalation Using an Oxygen Concentrator in Low-Pressure Environment Outside of a Hospital", The American Journal of Emergency Medicine, vol. 26, Issue 9, p. 981-984, Nov. 1, 2008.
Oxygen Concentrator/SET, S0002047 Product Information.
Miller, GW and Fenner, JE. "A "Smart" Molecular Sieve Oxygen Concentrator with Continuous Cycle Time Adjustment", Air Force Materiel Command Brooks Air Force Base, Texas, Apr. 1996; Final Technical Paper for Period Oct. 1989-Oct. 1992.
Katz, et al., "An in silico analysis of oxygen uptake of a mild COPD patient during rest and exercise using a portable oxygen concentrator", International Journal COPD, 2016:2427-2434.
Hardavella, et al., "Oxygen Devices and Delivery System", Breathe, Sep. 2019, vol. 15, No. 3.
Williams, Paul Robert, "Characterization and Feasibility of a Portable Oxygen Concentrator for use with a Mass Casualty Ventilator", thesis for Boise State University, Dec. 2013.
Driscoll, et al., "Emergency Oxygen Therapy for the COPD Patient", Emerg Med J 2001; 18:333-339.
Brill, et al, "Oxygen Therapy in Acute Exacerbations of Chronic Obstructive Pulmonary Disease" International Journal of COPD, 2014:9, 1241-1252.

* cited by examiner

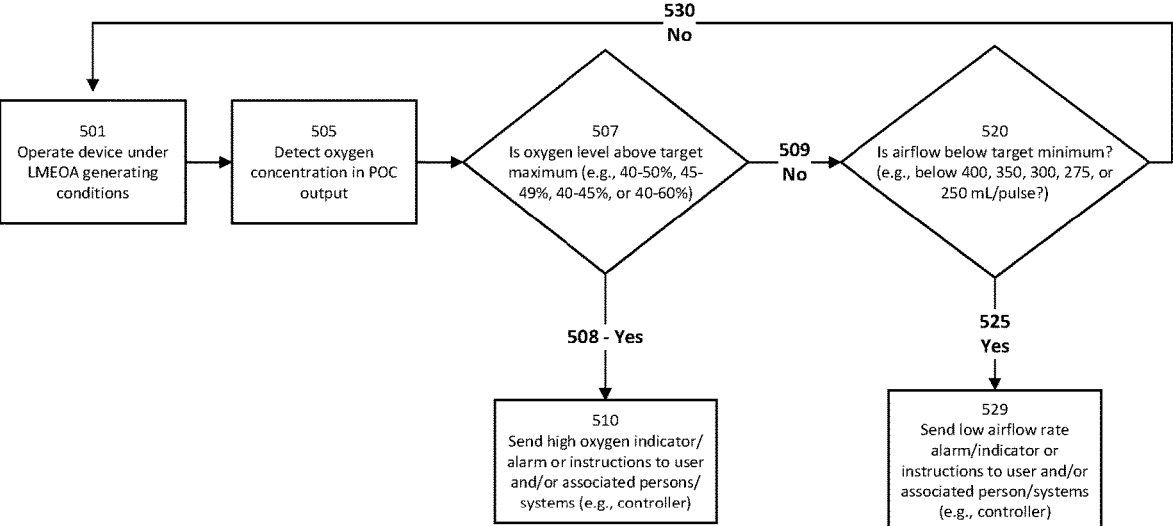

530
No

| 501 | 505 | 507 | 509 | 520 |
|-----|-----|-----|-----|-----|
| Operate device under LMEOA generating conditions | Detect oxygen concentration in POC output | Is oxygen level above target maximum (e.g., 40-50%, 45-49%, 40-45%, or 40-60%) | No | Is airflow below target minimum? (e.g., below 400, 350, 300, 275, or 250 mL/pulse?) |

508 - Yes

510
Send high oxygen indicator/ alarm or instructions to user and/or associated persons/ systems (e.g., controller)

525
Yes

529
Send low airflow rate alarm/indicator or instructions to user and/or associated person/systems (e.g., controller)

Figure 5

EFFICIENT ENRICHED OXYGEN AIRFLOW SYSTEMS AND METHODS

CROSS-REFERENCE TO RELATED APPLICATIONS

This application is a continuation-in-part of U.S. Non-Provisional patent application Ser. No. 17/850,804 entitled "Efficient Enriched Oxygen Airflow Systems and Methods," filed Jun. 27, 2022 and issued as U.S. Pat. No. 11,951,260, which is a continuation of U.S. Non-Provisional patent application Ser. No. 17/141,085 entitled "Efficient Enriched Oxygen Airflow Systems and Methods", filed Jan. 4, 2021, which claims priority to U.S. Provisional Patent Application No. 62/995,224, entitled "Method to Increase Blood Oxygen Concentration While Reducing Oxygen Concentrator Work," filed Jan. 21, 2020. This application claims the benefit of priority to, and incorporates by reference the entirety of, these above-referenced priority applications.

FIELD OF THE INVENTION

The invention relates to methods, devices, and systems for treating diseases, such as chronic obstructive pulmonary disease and related or similar conditions, through new and surprisingly effective methods and devices for the delivery of oxygen enriched airflows under conditions that are more efficient than current leading methods and devices for oxygen delivery.

BACKGROUND OF THE INVENTION

Hypoxemia is a condition characterized by low levels of oxygen in the blood, such as in the arteries. Hypoxemia occurs when the body's demand for oxygen exceeds the supply and the lungs are unable to replenish the oxygen, causing the oxygen level in the blood to fall below normal. Hypoxemia can arise from many factors including high altitude, heart disease, and respiratory problems, such as, e.g., chronic obstructive pulmonary disease ("COPD"), asthma, sleep apnea, cystic fibrosis, acute respiratory distress syndrome ("ARDS"), and lung disease.

Individuals whose blood oxygen levels are lower than normal often require the assistance of an external oxygen device to replace the oxygen. Generally, these devices are one of three types: oxygen cylinders, stationary oxygen concentration devices, or portable oxygen concentration devices ("portable oxygen concentrators" or "POCs"). Oxygen cylinders store a limited amount of pressurized oxygen, are quite heavy, and require frequent refilling and/or replacing. Oxygen concentrators, on the other hand, continuously bring in ambient air, compress and treat it, and then release the oxygen to the user. Portable oxygen concentrators purify and compress ambient air while removing nitrogen, converting the ambient air from the normal 21% oxygen to 90-95% pure oxygen. Unlike the cylinders, oxygen concentrators do not use a tank, and do not require refilling or replacing. Stationary oxygen concentrators (like oxygen cylinders) are useful when continuous oxygen flow is needed, such as when the user is sleeping or sitting still. When oxygen is administered via continuous flow, the flow rate remains the same regardless of the number of breaths or the deepness/force of the user's breaths.

As suggested by their name, portable oxygen concentrators are typically smaller, and more lightweight as compared to the stationary oxygen concentrators and have the added benefit of providing the user with freedom and mobility.

However, the amount of oxygen that can be produced by a portable concentrator over extended periods of time is limited due to energy requirements, size and weight of the compressor component, and battery life. Portable oxygen concentrators can be a continuous flow type or a pulse dose type (e.g., where oxygen is delivered to the user only when the user inhales). For an average person, if they take a breath approximately 20 times per minute ("breaths per minute" or "BPM"), this equates to about 1 breath every 3 seconds. One third of each breath taken is inspiration, so inspiration lasts for about 1 second. Therefore, if oxygen is only delivered to a person during inspiration, there is a 3:1 conservation ratio.

Oxygen concentrators are frequently associated with COPD patients. COPD is a group of chronic lung conditions, including emphysema and chronic bronchitis, that cause airways to become obstructed or blocked resulting in breathing-related issues. In chronic bronchitis, the bronchi (airways) become inflamed and irritated, causing them to fill with mucous and making it difficult for the lungs to bring in oxygen and rid carbon dioxide. In emphysema, the alveoli (air sacs) become irreparably damaged causing them to rupture, making a large air pocket instead of many smaller ones and causing air to become trapped in the damaged sacs while the lungs become overfilled. Both conditions cause air to be trapped in the lungs, thus preventing the lungs from fully emptying and causing the common symptoms of coughing, wheezing, excess phlegm and mucus, shortness of breath, and difficulty taking a deep breath.

COPD patients often have difficulty walking or climbing stairs and may have co-existing chronic conditions, such as arthritis, congestive heart failure, diabetes, coronary heart disease, stroke, and asthma. As a result, the challenges related to sufficient, portable oxygen supply for these patients are especially difficult, as the amount of oxygen a COPD patient needs is high, and with existing oxygen concentration systems, producing that much oxygen in a mobile device takes a lot of energy which means a big compressor and a heavier overall unit. Such large and heavy units are especially problematic for these patients, and this can create a downward spiral; COPD patients lack the mobile oxygen sources which can provide opportunities for movement; lack of movement can exacerbate poor breathing conditions e.g., due to lack of exercise.

Typically, patients receiving supplemental oxygen use a portable machine, which administers a pulsed flow of oxygen when the user is mobile, and a separate, larger stationary machine or oxygen tank administering continuous oxygen while the patient sleeps or is stationary at home. Continuous oxygen administration requires a substantial amount of work by the compressor and the machine in general, hence why these machines are bulkier and heavier.

The amount of oxygen delivered is of critical importance to patients that need enriched oxygen therapy, such as COPD patients. When a patient requires supplemental oxygen, the physician will prescribe a given oxygen flow rate, such as e.g., 2 liters per minute ("LPM"). 2 LPM of 90% oxygen equates with 37.1 ml/per breath (at a 20 breath per minute ("BPM") rate). Similarly, a prescription of 1 LPM at 90% oxygen equates with 18.6 ml/breath (at such rate), 3 LPM equates with 55.7 ml/breath, 4 LPM at 90% equates with 74.2 ml/breath, and 5 LPM at 90% equates with 92.8 ml/breath (at such rate).

Commercially available portable oxygen concentrators deliver highly enriched oxygen airflows, comprising 90%±3% oxygen concentrations. For example, Caire's portable FreeStyle Comfort delivers a recommended 90% (+5.5%/−3%) oxygen. Similarly, Caire's transportable Eclipse 5 also delivers a recommended 90% (+5.5%/–3%) oxygen, with a minimum oxygen concentration of 82%. Inogen's Inogen One G3, G4, and G5 models all deliver 90% (+6%/–3%) oxygen. Philips Respironics SimplyGo delivers at least 87% (and a maximum of 96%) oxygen. The Caire systems include an alarm to detect when the oxygen concentration dips below 85% after the warm-up period. Similarly, the Inogen systems produce an Oxygen Error when the oxygen output concentration has been below 50% for 10 minutes. The Philips SimpliGo also comes equipped with a low oxygen purity alarm.

U.S. Pat. No. 10,583,265 to Whitcher et al. discloses POCs with both pulse and continuous delivery where the system can measure the oxygen flow rate, pressure, and temperature, and based on the measurement, control the frequency and/or duration of the opening of the oxygen delivery valve.

Similarly, Japanese Pat. Appl. Pub. No. JP2008517638 to Bosinski et al. touches on the number of molecules of oxygen delivered per dose/inhalation, and how it is affected by the pressure and temperature of the gas. Wilkinson, mentioned above, also discloses the number of oxygen molecules in a given volume of air being increased by removal of heat from the compressed air.

Most patent and technical disclosures in the art also disclose the use of enriched oxygen airflows comprising at least 80% oxygen (see, e.g., U.S. Pat. Appl. Pub. No. 2011/0197890 (at least 85% oxygen concentration, and less than this amount will signal an error with the equipment), U.S. Pat. Appl. Pub. No. 2012/0000462 (describing enriched oxygen airflows containing 82-93% oxygen, using a system with an $O_2$ low alarm), U.S. Pat. Appl. Pub. No. 2006/0185668 (describing enriched oxygen airflows of 85-95%, also signaling an error when the concentrator fails to produce $O_2$ amounts of at least 85%), and Chinese Pat. Appl. Pub. No. CN202322372U (describing the desire to achieve oxygen concentrations of greater than 90%)). Enriching airflows to such high oxygen concentrations requires significant energy expenditure, limiting battery life and, accordingly, mobility, due to size/weight, and increased expense associated with operating such devices.

Several other patent documents and a few publications, however, make mention of enriched oxygen airflows with less than 80% or 90% oxygen concentration, although such statements are still exceptional in such patent documents and typically are made without details as to how such a system would be credibly operationalized. For example, U.S. Pat. No. 9,974,919 to Richard et al. ("Richard") (and related U.S. Pat. No. 9,974,918 to Armstrong et al. ("Armstrong")) is directed to portable oxygen concentrators that deliver oxygen via either continuous or pulse delivery. While nearly the entire focus of this patent is directed to reducing the energy consumption of the concentrators by using minimum oxygen purity levels of typically 85%-90% oxygen concentration, consistent with commercially known portable oxygen concentrators (which typically deliver about 90% oxygen), Richard includes a single statement that the purity level of the enriched oxygen airflow described therein could extend as low as 40% oxygen concentration, which contradicts the several other teachings in the document that point to use of oxygen airflows with concentrations in excess of 80%. Moreover, Richard provides no teaching concerning how such a system would be implemented, the effect on patients, etc. More relevant to patients, more than a decade after the first publication of Richard, there is no POC in the art that administers anything remotely close to a 40% oxygen concentration.

Further illuminating in this respect is the fact that Richard mentions a variable $O_2$ setting, that starts at 91% or higher on AC power, but can be lower on battery, e.g., 89% or lower, but that cannot extend so low that the device will trigger its $O_2$ Low Alarm. Notably, all of the portable and transportable systems manufactured by Caire, the assignee of the '919 and '918 patents, deliver oxygen in amounts of at least 87%. Caire's marketed systems also have a low oxygen concentration alarm. Such an alarm is triggered when the oxygen concentration falls below 85% after the warm-up period.

Canadian Pat. No. CA2810669 to Wilkinson et al. ("Wilkinson") describes oxygen concentrator systems, including portable oxygen concentrators, and defines oxygen-enriched gas as composed of amounts of oxygen as low as 50%, and as high as at least 99%. Wilkinson provides no mention of how a system producing oxygen in an amount of at least about 50% may function and how, or even if, it may be effective for COPD patients.

*Characterization and Feasibility of a Portable Oxygen Concentrator for use with a Mass Casualty Ventilator*, a thesis by Paul Robert Williams, published December 2013 (the "Williams Thesis"), suggests that such high purity oxygen may not be required in all instances, and that one might consider reducing compressor capacity, or modifying compressor settings to provide only a level of purity needed to maintain oxygen levels in the patient. The Williams Thesis mentions that one could increase flow rate, produce more oxygen, but deliver at a lower concentration of oxygen (<90%), and contemplates modifications of an existing system(s) from pulse to continuous flow. Most of the Williams Thesis focuses on adapting an existing POC and combining with a mass casualty ventilator in preparation for pandemic emergencies, and does not suggest how, if at all, the suggested machine could function as a long-term solution for chronically ill COPD patients. More than seven years after its publication, the Williams Thesis does not appear to have had an impact on how commercial POCs are designed or operate, suggesting that the art did not find the Williams Thesis to be credible in respect of such speculative statements. The work in the Williams Thesis also does not appear to have been the basis of any related or further patent or literature disclosures, reflecting a lack of motivation in the art to adopt or modify this work.

As of today, limited or no options exist for treating patients with especially advanced breathing difficulty, such as occurs in COPD, with enough oxygen to provide a therapeutic effect, while doing so in a manner that is efficient enough to extend the efficiency and, thus, e.g., the battery life of most POCs (e.g., beyond 1-1.5 days). Clearly, given the significant interest in the art in such improvements, achieving practical systems that can safely and effectively deliver oxygen that patients, such as COPD patients, require, while reducing the energy expenditure of such units, will require the application of inventive ingenuity.

Construction, Definitions, & Abbreviations

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects, as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading apply to other aspect(s) provided elsewhere.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a method or device comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01) (e.g., common tests used in such contexts in the art (e.g., for efficacy by clinical study)). "Detectable" means measurably present/different using known/described detection tools/techniques. "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or method), implicitly provides support for any detectable amount/number or $\geq\sim1\%$, $\geq\sim5\%$, $\geq\sim10\%$, $\geq\sim20\%$, $\geq\sim25\%$, $\geq\sim33\%$, $\geq\sim50\%$, $\geq\sim51\%$, $\geq\sim66\%$, $\geq\sim75\%$, $\geq\sim90\%$, $\geq\sim95\%$, $\geq\sim99\%$, or $\sim100\%$ of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing $\geq\sim1\%$, $\geq\sim5\%$, $\geq\sim10\%$, $\geq\sim20\%$, $\geq\sim25\%$, $\geq\sim33\%$, $\geq\sim50\%$, $\geq\sim51\%$, $\geq\sim66\%$, $\geq\sim75\%$, $\geq\sim90\%$, $\geq\sim95\%$, $\geq\sim99\%$, or $\sim100\%$ of the effect/outcome, representing $\geq\sim1\%$, $\geq\sim5\%$, $\geq\sim10\%$, $\geq\sim20\%$, $\geq\sim25\%$, $\geq\sim33\%$, $\geq\sim50\%$, $\geq\sim51\%$, $\geq\sim66\%$, $\geq\sim75\%$, $\geq\sim90\%$, $\geq\sim95\%$, $\geq\sim99\%$, or $\sim100\%$ of the steps/effort performed, or both. Explicit listing of percentages of elements/steps in connection with aspects does not limit or contradict such implicit disclosure. Uncontradicted, terms such as "comprising" when used in connection with a step of a method provide implicit support for performing the step once, $\geq2$ times, or until an associated function/effect is achieved.

Uncontradicted, the term "one" means a single type, single iteration/copy/thing, of a recited element or step, or both, which will be clear from context. For example, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a method/system).

The term "some" means $\geq2$ copies/instances or $\geq5\%$ of a listed collection/whole is, or is made up of, an element. Regarding methods, some means $\geq5\%$ of an effect, effort, or both, is made up of or is attributable to a step (e.g., as in "some of the method is performed by step Y") or indicates a step is performed $\geq2$ times (e.g., as in "step X is repeated some number of times"). "Predominately," "most," or "mostly," means detectably $>50\%$ (e.g., mostly comprises, predominately includes, etc., mean $>50\%$) (e.g., a system that mostly includes element X is composed of $>50\%$ of element X). The term "generally" means $\geq75\%$ (e.g., generally consists of, generally associated with, generally comprises, etc., means $\geq75\%$) (e.g., a method that generally consists of step X means that 75% of the effort or effect of the method is attributable to step X). "Substantially" or "nearly" means $\geq95\%$ (e.g., nearly all, substantially consists of, etc., mean $\geq95\%$) (e.g., a collection that nearly entirely is made up of element X means that at least 95% of the elements in the collection are element X). Terms such as "generally free" of an element or "generally lacking" an element mean comprising $\leq\sim25\%$ of an element and terms such as "substantially free" of an element mean comprising $\leq\sim5\%$ of an element. The term "substantially" in other context (e.g., when used in connection with tests or comparisons or as used in a phrase such as "substantially identical" or "substantially similar") typically is recognized as meaning not differing in any material way from the referenced element(s)/comparison (e.g., having essentially the same elements, amounts, and conditions in all material respects, except for any indicated differences, such as an explicitly referenced test condition, element, or agent).

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X. Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a method/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

The following table lists abbreviations of technical elements that are frequently used in this disclosure and provides a description of the general meaning thereof which may be supplemented by knowledge of skilled persons.

TABLE 1

Abbreviations

| Abbreviation | Term | Brief Description |
|---|---|---|
| ARDS | Acute respiratory distress syndrome | Respiratory failure characterized by widespread lung inflammation |
| BiPAP | Bilevel Positive Airway Pressure | A machine like a CPAP, but with separate pressure settings for inhalation and exhalation |
| COPD | Chronic obstructive pulmonary disease | A group of chronic lung conditions, that cause obstructed or blocked airways |
| CPAP | Continuous Positive Airway Pressure | Machine that increases air pressure in the throat to assist patients with obstructive sleep apnea breathe more easily during sleep |
| EOA | Enriched oxygen airflow | Airflow that has a higher concentration of oxygen than is found in ambient air |
| HEOA | Highly enriched oxygen airflow | Airflow that has an oxygen concentration of at least about 90% |
| HMEOA | High moderately enriched oxygen airflow | Airflow that has an oxygen concentration of about between 40-49% |
| IEOA | Intensively enriched oxygen airflow | Airflow that has an oxygen concentration of about 60-90% |
| LMEOA | Low moderately enriched oxygen airflow | Airflow that has an oxygen concentration of about between 30-39% |
| LTOT | Long-Term Oxygen Therapy | Treatment used to improve survival in COPD patients with chronic respiratory failure |
| MEOA | Moderately enriched oxygen airflow | Airflow that has an oxygen concentration of about between 30-49% |
| NAM | Nitrogen adsorption media | Media that removes nitrogen from ambient air to yield an enriched oxygen airflow |
| PC | Programmable controller | A controller that contains programmable stored computer readable instructions and a processor for executing such instructions and means for controlling operation of system component(s) |
| PGGS | Pressure gradient generating system | System for generating a pressure gradient to apply to the nitrogen adsorption media |

TABLE 1-continued

Abbreviations

| Abbreviation | Term | Brief Description |
|---|---|---|
| POC | Portable oxygen concentrator | A lightweight, battery-powered device for providing supplemental oxygen to a patient |
| PODI | Patient oxygen delivery interface | A device that facilitates administration of an airflow to a patient |

SUMMARY OF THE INVENTION

The invention described here provides new methods and devices for more efficiently delivering surprisingly effective amounts of oxygen to a mammalian subject, such as a person, such as a subject experiencing hypoxemia or other related disease or condition, such as a COPD patient, e.g., a COPD patient having low blood oxygen saturation as compared to typical normal levels.

The methods of the invention typically comprise administration of therapeutic amounts of one or more enriched oxygen airflows that are not highly enriched or intensively enriched oxygen airflows (as such airflows are described further herein), but comprise, mostly comprise, generally consist of, substantially consist of, or consist of moderately enriched oxygen airflows that surprisingly nonetheless deliver enough oxygen to the subject to achieve a desired physiological effect, treat a disease or condition, prevent the progression or occurrence of a disease/condition, or any or all of the above. In aspects, the moderately enriched airflows (MEOA) delivered to the subject can be/comprise high moderately enriched airflows (HMEOA) or low moderately enriched airflows (LMEOA) (e.g., in aspects methods comprise/systems deliver both LMEOA and HMEOA and, at times/under conditions can comprise delivering more enriched oxygen airflows, such as HEOA or IEOA). In aspects, ≥2 of an LMEOA, ≥2 of an HMEOA, or ≥2 of each type of airflow are administered to a patient by a system or method. E.g., methods can comprise calibrating MEOA in patients, or methods can comprise applying different MEOAs in response to conditions in the recipient/patient, etc.

In an aspect of the invention, the present methods comprise providing a human patient, such as a COPD patient or chronic hypoxemia patient, with a portable oxygen concentrator ("POC") that is configured to (I) deliver to the patient a therapeutic amount of one or more enriched oxygen airflows comprising an oxygen concentration of less than 50%, such as about 30-49% (an MEOA), e.g., an LMEOA comprising about 30-39%, such as about 31-38%, such as about 32-37%, such as about 33-36%, or such as about 34-35% oxygen concentration, or an HMEOA (comprising about 40-49%, such as about 41-48%, such as about 42-47%, such as about 43-46%, or such as about 44-45% oxygen concentration) in association with most, at least generally all, or at least substantially all breaths of such patient over a sustained period (e.g., at least 1, at least 3, at least 6, at least 12, at least 18, at least 24, or at least 30 months) and (II) deliver the enriched oxygen airflow(s) to the patient, in an average amount of oxygen molecules per patient breath (inspiration) that is about the same as or statistically similar to the amount of oxygen molecules delivered by a typical portable oxygen concentrator (POC) that delivers a highly enriched oxygen airflow (HEOA) of at least about 90%. Terms such as typical POC or POC adapted to deliver HEOA comprise devices such as those commercial devices described in the background (e.g., the Inogen One® G series devices). In another aspect, such a method further includes monitoring one or more conditions in the patient, such as breathing of the patient through a patient oxygen delivery interface ("PODI") (e.g., a nasal canula), as detected by one or more sensors or techniques, and changing the oxygen concentration of the enriched oxygen airflow ("EOA") delivered to the patient based on such conditions from an MEOA to an HEOA or an IEOA, or vice versa based on such conditions. In aspects, such a determination is made by a programmable controller that automatically controls operational component(s) of an enriched oxygen airflow delivery system(s) that generates the EOA, delivers the EOA(s) to the patient, or both. In aspects, computer systems that control such operations are directed by, e.g., machine learning or artificial intelligence based on outcome data derived from a sufficiently powered population of such patients, animal model subjects, in vitro modeling, in silico modeling, or a combination of any or all thereof.

In an aspect, the invention provides a method that comprises providing a human patient, such as a COPD patient or chronic hypoxemia patient, with a POC that selectively delivers one or more enriched oxygen airflows to the patient and that comprises (1) a pressure gradient generating system ("PGGS"), (2) at least one nitrogen adsorption media ("NAM") that generates an enriched oxygen airflow when exposed to air and acted on by a sufficient pressure gradient and that is selectively isolated from the environment by at least one air enrichment area separator, (3) an enriched oxygen airflow outlet that is fluidly connected to a flow line and a patient oxygen delivery interface (such as a nasal cannula), (4) a programmable controller ("PC") comprising stored (and programmable) computer readable instructions and a processor for executing such instructions and that in operation determines (I) the volume of the airflow delivered to the patient, (II) the oxygen concentration of the airflow, and (III) whether to deliver enriched oxygen airflow to a patient via continuous delivery or pulse delivery, and (5) one or more sensors configured to detect changes in the patient, such as changes in patient oxygen intake (e.g., at least one breath/breathing rate sensor), where the delivery of the enriched oxygen airflow comprises (I) generating an MEOA comprising an oxygen concentration of less than 50%, such as about 30-49%, e.g., an LMEOA comprising about 30-39%, such as about 31-38%, such as about 32-37%, such as about 33-36%, or such as about 34-35%, or an HMEOA comprising about 40-49%, such as about 41-48%, such as about 42-47%, such as about 43-46%, or such as about 44-45% and (II) pulse delivering the MEOA to the patient, in an effective amount per pulse (or per average pulse or generally all pulses) (e.g., about 80-about 600 mL of a MEOA per inspiration, such as about 80-about 240 mL such as about 90-230 mL, such as about 100-220 mL, such as about 110-210 mL, such as about 120-200 mL, such as about 130-190 mL, such as about 140-180 mL, such as 150-170 mL, such as about 280-540 mL, such as about 300-520 mL, such as about 320-500 mL, such as about 340-480 mL, such as about 360-460 mL, such as about 380-440 mL, such as about 400-420 mL, such that, in aspects, the average millimoles (mmol) of oxygen delivered to the patient per inspiration of the MEOA is about the same as or statistically similar to the amount of millimoles of oxygen (number of oxygen gas atoms) delivered to the patient per inspiration of a highly enriched oxygen airflow having an oxygen concentration of at least about 90%. In aspects the MEOA can be an LMEOA or an HMEOA. Such a method can further include the steps of automatically changing between continuous delivery and pulse delivery based on one or more patient characteristics detected by the system (when the controller determines that one or more aspects of the patient's breathing exceeds one or more pre-programmed thresholds), such as the patient's breathing rate, breathing volume, blood oxygen level, or other characteristic(s) detected by sensor(s). Monitoring of characteristics in a patient can comprise, e.g., monitoring breathing of the patient through the patient oxygen delivery interface ("PODI"), such as a nasal enriched oxygen airflow cannula. In AOTI, a change from pulse to continuous delivery is associated with a change in delivery of an MEOA to an HEOA/IEOA.

In another aspect, methods/systems of the invention ("methods/systems") (the term "systems" herein encompasses both POCs and more complex systems comprising elements of a POC as described herein) comprise applying any one or more of the conditions that deliver an amount of oxygen set forth in Table 2.

TABLE 2

| | | LPM | | | |
| | | 4 | 5 | 6 | 7 |
|---|---|---|---|---|---|
| O$_2$ | 30% | 283.90 ml | 354.88 ml | 425.85 ml | 496.83 ml |
| concentration | 40% | 387.53 ml | 473.17 ml | 567.80 ml | 662.43 ml |

The values in Table 2 assume a recipient with a breath rate of 12 BPM. In aspects, the invention provides systems/methods in which values of one or more elements of Table 2 are adjusted for patient BPMs of 10, 11, 13, 14, 15, 16, 17, 18, 19, 20, 21, 22, 23, 24, or 25 BPM or any range defined by any combination of such numbers (e.g., by reducing values by about $1/12^{th}$ to adjust for a 13 BPM rate of breathing).

In one aspect, methods/systems can comprise delivering a volume of enriched air that is about 65-135%, 75-125%, 85-115%, or 90-110% of a value provided in Table 2. In aspects, methods/systems comprise delivering 65-95%, 75-95%, 80-95%, or 90-95% of any such volume, or 65%-80% or 70-85% of any such volume(s). In aspects, methods/systems comprise delivering 105-175%, 105-150%, 105-135%, 105-125%, 110-150%, 110-140%, 110-160%, 115-145%, 115-135%, or 110-130% of any such volume(s).

In one aspect, methods/systems can comprise applying an approximately similar amount to any one of the amounts provided in Table 2. E.g., in aspects the invention provides methods/systems in which the EOA delivered is within +/−20%, +/−15%, +/−10%, or +/−5% of what is provided in Table 2 in terms of any one or more of the value combinations/values provided therein.

In an aspect, methods/systems comprise delivering amount(s) that are statistically significantly similar to amount(s) listed in Table 2, in respect of one or more outcomes (e.g., health-related outcomes as may be determined in an adequate, sufficiently powered, and well controlled clinical study as may be suitable for regulatory authority approval in the USA).

The invention also provides methods/systems comprising performing within any combination of conditions described in Table 2 (or approximate values related thereto). E.g., at the same 12 BPM if the O$_2$ concentration is at a value of 35%, at 4 LPM the amount administered would be 324.46 ml (about 325 ml) at 4 LPM, 405.57 ml at 5 LPM, 486.69 ml (about 485 ml) at 6 LPM, and 567.8 ml (about 570 ml) at 7 LPM. Again, these approximate values can be modified to accommodate lower or higher BPM (e.g., these values or any of the other values that can be delivered from these values according to the principles provided in the last few paragraphs of this disclosure can be decreased by about 25% to accommodate a patient with a breathing rate of about 15 BPM).

In a further aspect, the POC comprises an alarm component that is triggered when the oxygen concentration changes from MEOA to HEOA/IEOA oxygen. In aspects, moderately enriched airflows can be high moderately enriched airflows or low moderately enriched airflows. The alarm can be any type of alarm known in the art, including a beep, siren, buzz, or other sound, visual display, tactile output, or combination thereof, which is suitable for alerting users in the case of an alarm condition. In aspects the alarm can link with an app such as on a mobile phone in order to connect with additional individuals such as a caretaker, nurse, physician, healthcare monitoring service, clinical trial manager, facility manager, family member, etc. (e.g., transmitting messages to 2, 3, 4, 5, or more accounts).

In a further aspect, the invention provides a method wherein in some, most, generally all, or all (SMGAOA) cases of continuous delivery the POC delivers about 240-640 mL of an IEOA or HEOA to the patient, e.g., about 260-620 mL, e.g., about 280-600 mL, such as about 300-580 mL, such as about 320-560 mL, such as about 340-540 mL, e.g., about 350-550 mL, about 350-530 mL, about 350-520 mL, such as about 360-520 mL, such as about 380-500 mL, e.g., about 390-470 mL, such as about 400-480 mL of either an intensively enriched oxygen airflow or highly enriched oxygen airflow.

In another aspect, the invention provides methods wherein the POC switches from pulse delivery to continuous delivery or vice versa at least once per day (e.g., per 24-hour interval) on average during a treatment period of ≥1, ≥3, ≥6, ≥12, or ≥18 months, e.g., based on automatic operation of a controller component (e.g., a software component that acts on recipient-related data collected by sensors or other devices, including, e.g., health care monitoring devices such as a smart watch (e.g., an Apple Watch, FitBit, or a similar device, or a device that is adapted to performing similar monitoring for sensitive health related conditions).

In another aspect, the invention provides a method further comprising automatically changing the POC's airflow from an MEOA to an intensively enriched oxygen airflow or highly enriched oxygen airflow based on the detection of one of more conditions comprising one or more breath/breathing rate conditions in the patient. In aspects, the change is made automatically by a PC in response to signals from one or more sensors meeting or exceeding threshold(s) associated with physiological condition(s). In response, users of such devices are given the ability to change to delivery of HEOA through an associated mobile app, control on the device, or both.

In another aspect, a method of the invention further comprises automatically changing the airflow from an intensively enriched oxygen airflow or highly enriched oxygen airflow to a moderately enriched oxygen airflow based on the detection of one or more conditions comprising one or more breath/breathing rate conditions in the patient. In aspects, the moderately enriched airflow can be high moderately enriched airflow or low moderately enriched airflow.

In another aspect, the invention provides a method wherein the average rate of enriched airflow to the patient in continuous delivery, pulse delivery, or both, is at least about 3.3 LPM. In aspects, the average rate of enriched airflow to the patient in continuous delivery, pulse delivery, or both, is greater than about 3.6 LPM, such as 4 LPM, such as 5 LPM, such as 6 LPM, such as 7 LPM, or greater (e.g., 4-7 LPM, 5-7 LPM, 4-8 LPM, 4-10 LPM, 4-9 LPM, 5-9 LPM, 5-10 LPM, 5-8 LPM, 5-7 LPM, 6-9 LPM, 6-10 LPM, 6-8 LPM, 6-7 LPM, 5-7 LPM, or about 6, about 7, or about 5 LPM).

In another aspect, the invention provides a method wherein the average oxygen intake per patient inspiration is about 0.05 mmol-about 0.5 mmol oxygen.

In another aspect, the invention provides a method wherein the method comprises operating the pressure gradient system at least about 33% longer (e.g., ≥40%, ≥50%, ≥75% longer, or 100% longer (i.e., at least twice as long as), opening the air enrichment area separator at least about 33% longer (or for similar increases as those described in the preceding clause), or both, as compared to the default operating parameters of a commercially available POC producing HEOA, such as an Inogen One® G3, Inogen One® G4, or Inogen One® G5 POC. Those of skill in the art will recognize that such devices refer to such devices as sold and approved under applicable regulatory market authorizations on Jul. 20, 2022. Thus, while such devices may be referred to by brand name, this is for convenience, and it will be understood that such references are to such actual devices and devices according to such regulatory authorizations (e.g., Inogen One POCs have market authorization under a 510(k) associated with FDA Regulation Number 868.5440 and 510(k) number K032818). Similar 510(k) numbers for the other devices described by name herein are known in the art and are to be deemed incorporated herein by reference to such brand names. In aspects, systems/methods of the invention are characterized by the exclusion of one or more non-essential elements of any of the systems/methods described in the patent documents provided in the Background of this disclosure (e.g., by excluding elements of the Armstrong reference that do not correspond to any elements described herein or that differ from the elements described herein). For example, the POC ashtray feature of Armstrong can be excluded from any aspect, as can any alarm in Armstrong that is associated with falling below a HEOA/IEOA-associated oxygen concentration or a concentration that is higher than an LMEOA range.

The POC of the present invention can be configured to deliver enriched oxygen according to a target profile, which can be defined by, e.g., one or more target characteristics (e.g., a target oxygen concentration, oxygen concentration range, volume of air delivered, etc.). In an exemplary aspect, the target profile comprises an oxygen concentration of 30-39% (LMEOA). In aspects, the POC delivers EOA within about +/−5% of the target profile for a period that is significantly longer than the period provided by a POC that is configured to deliver HEOA, such as an Inogen One® POCs. In aspects, the POC delivers EOA that remains within 15%, within 10%, within 8%, within 5%, within 2.5%, or within about 1% of the target profile for a period of at least about 3, 6, 9, 12, 18, or 24 months, or 30 months, 36 months, 42 months 48 months, or longer.

In another aspect, the invention provides a method wherein the nitrogen adsorption media comprises sieve beds that are configured to maintain the therapeutic level of oxygen for a period of time that is greater than 1 year, such as greater than 18 months, such as greater than 2 years, such as greater than 3 years, such as greater than 4 years, such as greater than 5 years.

In another aspect, POCs of the invention are capable of maintaining an average level of oxygen (e.g., 30-39%, 30-49%, 30-50%, 40-59%) for a period of time that is greater than 1 year, such as greater than 18 months, such as greater than 2 years, such as greater than 3 years, such as greater than 4 years, such as greater than 5 years, or that is significantly longer than the period of time that a HEOA POC, such as an Inogen One POC, can maintain within +/−10%, 5%, or 2.5% of its label/nameplate oxygen concentration.

In a further aspect, the invention provides a method wherein the method comprises applying a pressure gradient comprising a maximum pressure of about 10-about 30 PSI to the nitrogen adsorption media.

In a further aspect, the invention provides a method wherein the delivery of oxygen consumes an average of between about 30-90 Watts of energy, such as between about 30-80, 30-70, or 30-60 Watts (e.g., 40-90, 45-90, 50-90, 40-80, 45-80, 35-75, 45-75, or 55-75 Watts).

In a further aspect, the invention provides a method wherein the concentration of oxygen in MEOA(s) delivered to the patient in the method is about 40%, such as 38-42%, e.g., 39-41%, or 39.5-40.5%, and the average volume of moderately enriched airflow delivered per inspiration is between about 280 mL to about 600 mL, such as about 300-580 mL, such as about 320-560 mL, such as about 340-540 mL, such as about 360-520 mL, such as about 380-500 mL, or such as about 400-480 mL. In aspects the MEOA(s) delivered can be HMEOA(s) or LMEOA(s).

In another aspect, the invention provides a method wherein the average volume of moderately enriched airflow delivered per inspiration thereof is at least about 300 mL. In aspects, the average volume of MEOA(s) delivered per inspiration in one or more modes of POC operation is ≥~400 mL. In aspects the MEOA(s) can be LMEOA(s) or HMEOA(s).

In another aspect, the invention provides a method wherein the patient has an average blood oxygen saturation of lower than about 93% or 92%, such as about 88%-92%, at the initiation of the method.

In a further aspect, the invention provides a method wherein the method comprises testing the patient for tolerance of moderately enriched oxygen airflow under supervision of a healthcare provider before allowing the patient to self-manage the portable oxygen concentrator.

In a further aspect, the invention provides a method wherein the portable oxygen concentrator generates an average of less than ~50, ~40, ~35, or less than ~30 decibels of noise during most, generally all, substantially all, or all periods of operation.

In a further aspect, the invention provides a method wherein the method is performed for a period of at least about 6 months, such as for at least 9 months, such as for at least 12 months, such as for at least 18 months, such as for at least 24 months, or such as e.g., ≥~30 months.

In a further aspect, the invention provides a method wherein airflow(s) delivered to the patient consists essentially of oxygen enriched air (e.g., in being free of active pharmaceutical agent(s), gasses not found in normal atmospheric air, additional moisture, or a combination thereof). In aspects, application of the method is the primary method employed to relieve temporary breathing conditions in the subject/patient.

In aspects, any of the above-described methods comprises a step of monitoring the patient for an initial testing period to assess the suitability/effectiveness of delivering MEOA(s) to the patient for some, most, generally all, or all the oxygen delivery period of each day, typically over a treatment period (e.g., ≥2 days, ≥4 days, ≥5 days, ≥7 days, ≥2 weeks, or ≥1 month). In aspects, such tests are conducted under the supervision of a health care provider prior to permitting the patient to self-manage the POC/delivery of oxygen.

The invention also provides new systems capable of delivering an effective and efficient moderately enriched oxygen airflow ("MEOA") and that can perform any of the above-described methods in this Summary. In aspects the MEOA can be an LMEOA or an HMEOA.

In one such exemplary aspect, the invention provides a system comprising a portable oxygen concentrator comprising (a) a pressure gradient generating system, (b) at least one nitrogen adsorption media configured to generate an enriched oxygen airflow when exposed to air and acted on by a sufficient pressure gradient and that is selectively isolated from the environment by at least one air enrichment area separator, (c) an enriched oxygen airflow outlet that is fluidly connected to a flow line and a patient oxygen delivery interface, (d) a programmable controller comprising stored computer readable instructions and a processor to determine (1) the volume of the airflow delivered to the patient, (2) the oxygen concentration of the airflow, and (3) to cause delivery of enriched oxygen airflow to a patient either via continuous or pulse delivery, and (e) one or more sensors configured to detect changes in patient oxygen intake, such as at least one breath/breathing rate sensor, wherein in operation (1) the controller controls the operation and operating conditions of the pressure gradient generating system, the at least one air enrichment area separator, the enriched oxygen airflow outlet, and the oxygen delivery interface, (2) the one or more sensors are configured to monitor breathing of the patient through the oxygen delivery interface and determine whether one or more aspects of a user's breathing exceeds one or more pre-programmed thresholds, (3) the controller causes the delivery of enriched oxygen to change from a pulse delivery to a continuous delivery and back again based on whether the breathing of the patient exceeds the one or more pre-programmed thresholds, and (4) in pulse delivery the system generates and delivers a moderately enriched oxygen airflow comprising less than 50%, such as about 30-49%, e.g., an LMEOA comprising about 30-39%, such as about 31-38%, such as about 32-37%, such as about 33-36%, or such as about 34-35%, or an HMEOA comprising about 40-49%, such as about 41-48%, such as about 42-47%, such as about 43-46%, or such as about 44-45% in pulses that administer about 80-about 600 mL per inspiration, such as about 80-about 240 mL such as about 90-230 mL, such as about 100-220 mL, such as about 110-210 mL, such as about 120-200 mL, such as about 130-190 mL, such as about 140-180 mL, such as 150-170 mL, such as 280-540 mL, such as 300-520 mL, such as 320-500 mL, such as 340-480 mL, such as 360-460 mL, such as 380-440 mL, such as 400-420 mL.

In aspects, the POC is configured to deliver to the patient about 240-640 mL of intensively enriched airflow wherein the intensively enriched oxygen airflow comprises 60-90% oxygen, a highly enriched oxygen airflow (comprising ≥~90% oxygen), or both, typically under continuous flow conditions.

In one aspect, the invention provides a system wherein the POC also is configured to switch from pulse delivery to continuous delivery, from continuous delivery to pulse delivery, or any combination thereof, at least once per day (e.g., per 24-hour interval) on average, over a period of treatment (e.g., ≥~1 month, ≥~3 months, ≥~6 months, ≥~12 months, or ≥18 months). In one aspect, the POC also (i.e., also or alternatively) is configured to change the airflow from the MEOA to the IEOA/HEOA, from IEOA or an HEOA to an MEOA, or any combination thereof, based on the detection of one of more conditions in the patient/ subject, such as rate of breathing, determined by sensor(s) of the system or that are operatively linked to the system (e.g., by a shared electronic medical record). In one aspect, the POC is configured to deliver an average rate of enriched airflow in continuous delivery, pulse delivery, or both, of at least about 3.3 L/minute or at least about 3.6 L/minute. In aspects, the system is configured to deliver an average volume of about 0.05 mmol to about 0.5 mmol of moderately enriched airflow, per inspiration of the patient. In aspects, the system is configured/adapted such that the pressure gradient applied to the nitrogen adsorption media comprises a maximum pressure of about 15-25 PSI. In aspects, operation of such a system in one or more modes of operation (or all modes of operation), on average, mostly, generally, substantially, or entirely consumes an average of about 30-90, such as 30-60 Watts of energy. In aspects, the system is configured to deliver an average volume of between about 150-350 mL (e.g., about 200 mL) of moderately enriched oxygen airflow per typical inspiration (e.g., as determined by clinical testing, modeling, consumer testing, or combination), in at least one mode, if not all modes of operation. A "mode" in this respect can be considered a setting in which the POC delivers a defined type of enriched oxygen airflow, such as one particular type of an enriched oxygen airflow, such as only MEOA (or separately only HEOA/IEOA), provided that the mode can include variations and transitions, such that it is possible to describe a mode as generally, substantially only, or essentially being associated with the referenced type of enriched oxygen airflow. In aspects, pulse delivery comprises more than one pulse delivery mode, each pulse delivery mode comprising different oxygen concentrations, different volumes of enriched oxygen airflow, or both. In other aspects, systems are configured to deliver an average volume of at least about 300 mL of moderately enriched airflow per inspiration of a typical patient in at least one mode (e.g., when delivering a moderately oxygen enriched airflow). In aspects, such a system can comprise a pressure gradient that operates on average, generally, substantially, or only at least about 33% longer; on average, generally, substantially, or only opening the air enrichment area separator at least about 33% longer; or both, as compared to the default operating parameters of a commercially available POC configured to deliver HEOA, such as an Inogen G3, Inogen G4, or Inogen One® G5 POC.

In another aspect, the invention provides a method wherein the nitrogen adsorption media comprises sieve beds that are configured to maintain the therapeutic level of oxygen for a period of greater than 1 year, such as greater than 18 months, such as greater than 2 years, such as greater than 3 years, such as greater than 4 years, such as greater than 5 years. In aspects the sieve beds of the present POC are configured such that the therapeutic value of the oxygen produced after passing through the sieve beds is maintained for a longer period of time as compared to a commercially available POC configured to deliver HEOA, such as an Inogen G3, Inogen G4, or Inogen One® G5 POC.

Such embodiments and additional aspects and features of the invention will be described further in the following Detailed Description of the Invention. To aid the reader, parts of the Detailed Description will focus on particular elements of the inventive systems or methods. However, unless otherwise indicated any aspect, feature, embodiment, component, step, or method of the invention can be combined with any other such aspect, feature, embodiment, component, step, or method, and the focus on the particulars of any aspect should not be interpreted as a limitation of any aspect, but, rather, as providing possible details for any such element, feature, step, etc., that can be combined with the various descriptions of inventive systems and methods provided herein, unless otherwise explicitly stated or clearly contradicted by context.

BRIEF DESCRIPTION OF THE DRAWINGS/FIGURES

FIG. 5 is a flowchart for the operation of a POC device in accordance with a non-limiting embodiment of the invention.

DETAILED DESCRIPTION OF THE INVENTION

Figure 1:
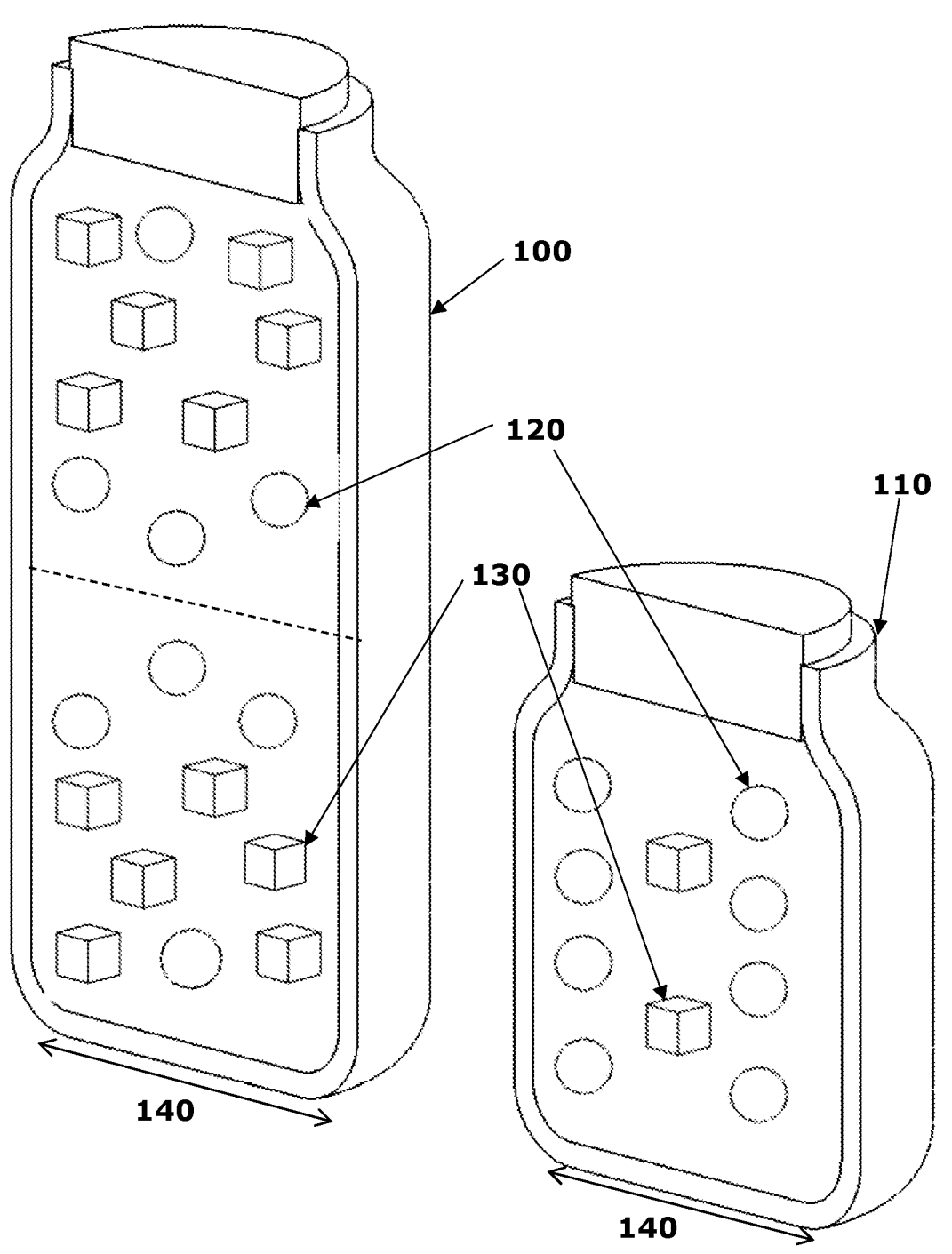
FIG. 1 is an abstract representation comparing the molar ratio of enriched oxygen molecules to total air volume delivered by a portable oxygen concentrator of the present invention compared to that of portable oxygen concentrators described in the prior art (delivering 80% enriched oxygen).

Described herein are new methods, devices, and systems for delivering oxygen to subjects (e.g., patients with a disease/condition associated with the need for enhanced oxygen intake for treatment or prevention of such a disease/ condition). Methods, devices and systems of the invention are characterized by the generation and delivery of moderately enriched oxygen airflow(s) to the subject/patient during period(s) of the treatment, under certain conditions in the patient, or both. In aspects, an MEOA is delivered consistently to the subject/patient in the method/system. In aspects, the method comprises switching, and the system is configured to switch, between mode(s) comprising delivery of MEOA(s) and mode(s) comprising delivery of IEOA(s), HEOA(s), or both, and back again based on one or more conditions, parameters, or a combination of both. In aspects MEOA can be LMEOA or HMEOA.

In one exemplary aspect, the invention provides a method of, and/or in aspects a system for, assisting breathing in a subject, such as a patient suffering from chronic obstructive pulmonary disease (COPD) (e.g., a COPD patient having a low blood oxygen saturation as described herein or in the art). In aspects, the method/system comprises providing the patient with a POC comprising (1) a pressure gradient generating system, (2) at least one nitrogen adsorption media, (3) an enriched oxygen airflow outlet that is fluidly connected to a flow line and a patient oxygen delivery interface (such as a nasal cannula), (4) a programmable controller comprising stored computer readable instructions and a processor for executing such instructions and that in operation determines (I) the volume of the airflow delivered to the patient, (II) the oxygen concentration of the airflow, and (III) whether to deliver enriched oxygen airflow to a patient via continuous delivery or pulse delivery, and (5) sensor(s) that detect change(s) in the patient related to oxygen intake/concentration in the patient. In aspects, the method further comprises delivering an enriched oxygen airflow to the patient for a sustained period (chronically)

(e.g., for a period of ≥~1 month, ≥~3 months, ≥~6 months, ≥~12 months, or ≥~18 months), by (1) generating a moderately enriched oxygen airflow comprising an oxygen concentration of less than 50%, such as about 30-49% (an MEOA), e.g., an LMEOA comprising about 30-39%, such as about 31-38%, such as about 32-37%, such as about 33-36%, or such as about 34-35%, or an HMEOA comprising about 40-49%, such as about 41-48%, such as about 42-47%, such as about 43-46%, or such as about 44-45% during one or more periods of treatment. In aspects, the method comprises pulse delivering to the patient about 80-about 600 mL of an airflow selected from one or more moderately enriched airflows per inspiration. In aspects, the average millimoles of oxygen delivered to the patient per inspiration is statistically similar to the average amount of millimoles of oxygen delivered to a similar patient or class of patients per inspiration of a highly enriched oxygen airflow ("HEOA") (e.g., comprising ≥87%, 88%, or 90% oxygen). In aspects, the method comprises monitoring one or more patient conditions relating to oxygen levels, oxygen intake, or an oxygen level/intake-related physiological parameter or health condition, and modifying the oxygen delivery volume, concentration, or both, to the patient based on the change in parameter(s). In one exemplary aspect, the parameter comprises oxygen concentration in the patient, breathing rate, breathing volume, or a combination thereof, and the method comprises automatically changing between continuous delivery and pulse delivery of enriched oxygen airflow(s) based on one or more parameter(s) detected by sensor(s) operatively associated with the POC reaching or exceeding one or more pre-programmed thresholds. In aspects, such a change in airflow occurs only upon validation of the meeting or exceeding of such threshold(s)/standard(s), such as when ≥2, ≥3, or ≥4 parameters are met/exceeded, a parameter is met or exceeded by ≥2 different sensor(s), a parameter is met/exceeded in 2 different readings, or a combination thereof.

In aspects, the POC can be equipped with an alarm component that can be configured to alert when the oxygen concentration changes from MEOA to HEOA/IEOA. In further aspects the alarm component can be triggered when the oxygen concentration exceeds the level typically associated with MEOA. In aspects the alarm component can be triggered when the oxygen concentration exceeds the level typically associated with IEOA/HEOA. In aspects the alarm is triggered when the oxygen concentration exceeds 50%, such as greater than 55%, such as greater than 60%, such as greater than 65%, such as greater than 70%, such as greater than 75%, such as greater than 80%, such as greater than 85%, such as greater than 90%, or even higher. In further aspects, the alarm is triggered when the administration of pulse delivered oxygen changes to administration of continuously delivered oxygen.

In an aspect, the POC is equipped with a manual shut off for the alarm feature, such as when the patient decides to manually change the administration to continuous flow, e.g., when preparing to go to sleep.

In another aspect, the POC can be equipped with one or more physiological sensors associated with the patient that can be monitored, recorded, and also can be linked to predetermined threshold values. In further aspects, the sensors can measure one or more of heartrate, pulse, body temperature, skin temperature, etc.

In another aspect, the controller can be programmed, upon activation of the alarm, to compare the readings of the one or more physiological sensors and compare the values to the predetermined threshold to see if the oxygen mode change is associated with a concerning value that may require sending a message to a healthcare provider or caretaker for assistance.

Various features of the inventive methods/systems are described in detail in the following sections, but readers will understand that this is for convenience only and any aspect described in connection with one element/step or characteristic/aspect can be combined with any other aspect, facet, or characteristic of the invention unless contradicted.

Subjects/Patients/Users and Associated Persons (e.g., HCPs)

Methods/systems of the invention can be adapted/applied to any suitable mammalian subject, including companion animals, livestock animals, laboratory animals, zoological animals, and humans. In aspects, the subject of a method or the subject for which a system is adapted to be applied to is a human patient, such as a human patient having or identified as being at risk of developing a disease/condition associated with low oxygen concentration, low oxygen intake, or both. In an exemplary aspect, the subject has blood oxygen levels which are reduced compared to normal human levels in one or more contexts, such as at rest, or, for example, such as an oxygen saturation level ($SpO_2$ level) of less than 95%, such as less than 93%, such as less than 92%, less than 91%, or less than 90%. In aspects, the subject is a patient diagnosed with a condition that requires the assistance of an external oxygen device to replenish oxygen levels. In aspects, the subject is an individual suffering from respiratory problems or diseases affecting their lung function or capacity. In aspects, the subject is a person diagnosed as suffering from one or more of: COPD, asthma, sleep apnea, cystic fibrosis, ARDS, or other lung/lung-related disease or condition. In aspects, the subject is a person diagnosed with COPD. In aspects, the subject is a person diagnosed with such condition(s) and having one or more related co-existing health conditions, such as arthritis, congestive heart failure, diabetes, allergic conditions, coronary heart disease, stroke, or asthma, or other condition(s) which further impact the subject's breathing, oxygen retention, or strength, mobility, or stamina. In aspects, the patient is a patient that has been diagnosed/approved for (prescribed) or has a condition typically associated with or requiring an oxygen delivery treatment protocol that would be recognized as a long-term oxygen therapy (LTOT).

POC and Enriched Oxygen Airflow Delivery

The POC component can be any suitable type of POC. Typically, the POC will be a relatively small, portable unit (e.g., having a weight of about 1.5-25 pounds, such as about 1.5-15 or 2-20 pounds, often about 2.5-10 pounds, 2-10 pounds, 2-8 pounds, 3-9 pounds, or 4-10 pounds). In aspects, the POC is about 2.5-15 inches in most or all dimensions (width, depth/length, and tallness/height). In aspects, 1, 2, or 3 of the dimensions are between ~1-12, ~1.5-10.5, ~2-12, ~3-12, ~3-9, ~2-10, or ~4-9 inches. The POC can be any suitable POC that has the capability to deliver the same amount of oxygen per inspiration at a significantly lower overall oxygen concentration (e.g., an oxygen concentration of 30-49%, such as 30-39%) than administered by typical commercial units configured to deliver HEOA, such as Inogen One® G Series POC units or other units on the market (i.e., an oxygen concentration of 90-95%).

In one aspect, the POC is an "enhanced POC." An enhanced POC is a POC that originally was produced without the ability to deliver an MEOA, without the ability to switch between an MEOA delivery mode and other modes, or both, but which is modified after initial configuration/operation to be able to deliver an MEOA to a patient, to switch between delivery of MEOA(s) and HEOA(s)/ IEOA(s), or both. In aspects, the MEOA that the POC is adapted to deliver by such a modification can be/comprise an LMEOA or an HMEOA. For example, in one exemplary aspect, an enhanced POC is obtained based on the modification of an Inogen One® G series POC that lacked such capabilities in original production specifications, when made available for sale, or sold, or both, and that is adapted through modification of, i.a., the POC's operating system to be able to perform the function(s) of the methods/systems of the invention. In aspects, the Inogen One® G series POC has been used for a period of time such that it no longer is able to achieve its advertised level of administered oxygen purity (HEOA) (e.g., varying by such levels of purity by a significant amount or by at least 5%, 10%, 15% or more, most of the time, generally all of the time, all of the time, or at least in most cases, generally all cases, or all cases (e.g., in a sampling of such devices)). In aspects, the period of time is about 3 months, or about 6 months, or about 9 months, or about 12 months. In aspects, the enhanced POC comprises the addition of one or more user accessible setting(s) not originally contained/programmed in the POC. E.g., in a POC initially having six different modes of operation, an enhanced POC state can comprise a $7^{th}$ setting, or $7^{th}$ and $8^{th}$ settings, or $7^{th}$, $8^{th}$, and $9^{th}$ settings, etc., reflecting modes in which an MEOA is delivered to the patient, typically at volumes higher than initial settings. In one aspect, the method provides a method of modifying an existing POC having an MEOA delivery functionality comprising changing the operating system of the POC to change the operational characteristics of oxygen enrichment (time of operation, pressure of operation, or both, or conditions/timing of contact with the NAM), oxygen airflow characteristics (typically increasing volume of oxygen delivered), or a combination thereof. In aspects, an enhanced POC also comprises a continuous delivery or pulse delivery mode where no such type of mode was present in the POC prior to enhancement. In an aspect, the invention provides a method of enhancing the functionality of a POC comprising providing the POC with the ability to apply MEOA(s) to a subject under conditions to deliver a statistically similar or approximately the same amount of oxygen per average patient inspiration as delivered by the POC using an HEOA under the delivery conditions used in current on-market POCs configured to deliver HEOA, such as the Inogen G Series POCs. In aspects, the enhancement of a POC comprises providing the POC with a controller that automatically changes from mode(s) to other mode(s), wherein at least some mode(s) comprise the application of MEOA(s). In aspects, one or more physical components of the system also are changed (e.g., by the addition of a blower to supplement or replace a compressor, by the addition of components that accommodate a greater volume of enriched oxygen airflow delivery to a patient, or both). In aspects, such modified components are provided to a user along with an operating system upgrade to arrive at an enhanced POC having any of the above-described functions. In aspects, enrichment of a POC comprises modifying battery settings to provide for the better efficiency of POC batteries associated with use of MEOAs.

Typical POCs function by collecting ambient air from the environment, which consists of about 80% nitrogen and 20% oxygen, compressing the ambient air, removing some/ most of the nitrogen from the airflow, and thereafter outputting an enriched oxygen airflow ("EOA"), and delivering the EOA to the patient through an interface, such as a nasal cannula. An EOA is an airflow that has a higher concentration of oxygen than is found in ambient air. For example, the system specifications for the Inogen One® G3 concentrator provides for an oxygen concentration of 87-93% at any of its 4 or 5 settings. Similarly, the Inogen One® G4 concentrator provides for an oxygen concentration of between 87-93% at any of its 3 settings. Further, the system specifications for the Inogen One® G5 concentrator provides for an oxygen concentration of between 87-93% at any of its 6 settings. An MEOA comprises a substantial reduction of oxygen concentration compared to, for example, the Inogen One® G5 concentrator, such as an oxygen concentration less than 49% or less than 40% (and typically greater than 30% or 31%, such as greater than 33%, such as greater than 37% or 38%, e.g., ~30-35%, ~30-37%, or about 30-38%~40-45%, ~40-47%, or about 40-48%).

An EOA can be classified as a highly enriched oxygen airflow ("HEOA") having an oxygen concentration of at least about 90% (such as in the Inogen One® series), an intensively enriched oxygen airflow ("IEOA") having an oxygen concentration of at least about 60% (but less than about 90%), or a moderately enriched oxygen airflow ("MEOA"), an airflow comprising an oxygen concentration typically of between about 30-49%, e.g., 30-35%, ~30-37%, or about 30-38%~40-45%, ~40-47%, or about 40-48%. In aspects, an MEOA can comprise or be characterized as an LMEOA or an HMEOA.

Readers should note that sometimes the word "oxygen" is used in place of EOA, as is typical in the art. Skilled persons will understand when such a use of "oxygen" in this disclosure or the art actually is in reference to an EOA, not pure oxygen. However, oxygen concentrations, by contrast, such as described in the preceding paragraph, refer to the concentration of oxygen within an enriched oxygen airflow.

Known oxygen concentrators in the market, such as the Inogen One®, are typically HEOA systems (delivering oxygen in concentrations of about 90% or more). Methods/ systems of the present invention, however, comprise the use of moderately enriched oxygen airflows (MEOA(s)) in one or more states of operation (modes). In aspects, methods/ systems of the invention are configured to switch between delivery of an MEOA, such as an LMEOA or an HMEOA under certain conditions and an HEOA, IEOA, or both, under other conditions.

In aspects, the POC on average, most of the time, at least generally always, at least substantially always, or always operates a volume of less than about 50 decibels, such as less than about 40 decibels, such as less than about 38 decibels, such as about 35 decibels or less, e.g., about 30 decibels or less. In aspects, the POC generates significantly less noise, generates noise significantly less frequently, or both, when operating under normal operating conditions as compared to on market POCs delivering HEOA, such as Inogen® POCs.

POCs typically comprise one or more battery units, which typically are rechargeable. In aspects, the battery life of a POC operating according to the invention will have a battery life that is ≥~20%, ≥~33%, or ≥50% longer than typical commercial POC batteries (e.g., having a typical 8-cell battery life or battery life in at least generally all or substantially all POCs of ≥5.5 hours, ≥~6 hours, ≥~6.5 hours, ≥~7 hours, per battery. In aspects, the POC will comprise multiple batteries or greater numbers of cells (e.g., 2, 3, or 4 batteries or ~12, 16, 24, or 32 cells, e.g., 6-36 cells or 8-24 cells, such as ~8-16 cells), and, accordingly, have an overall typical battery performance life (on average, generally in all devices, or substantially in all devices, for at least one of the treatment periods described here) of ≥~10 hours, ≥~12 hours, ≥~14 hours, ≥~18 hours, ≥~24 hours, ≥~30 hours, or ≥36 hours (without recharge). In aspects, the batteries of the portable oxygen concentrator require recharging on average less than every 15 hours. Typically, a battery can be recharged in about 2.5-5, 2-3.5, or 1.75-3/3.5 hours, and a collection of batteries can be recharged in 2.5-10, 3-8, 3.5-7.5, 3.5-7, 4-7, or 4-6 hours, using either AC or DC power. In aspects, POCs can be powered by AC power, DC power, or both, and in aspects can adapt to different power supplies (e.g., 100-240V, 50-60 Hz, based on sensor(s) that determine the type of direct power supply and adjust power parameters accordingly (e.g., for patients traveling between different countries). In aspects, the POC batteries can be charged while also operating (e.g., overnight). In aspects, the batteries comprise or consist of batteries contained in an external battery unit. In aspects, the external battery unit can be physically coupled to the POC. In aspects, the external battery unit can be linked to the POC by a flexible wire.

In further aspects, POCs of the invention are adapted to operate for a longer period of time than a conventional HEOA POC due to, inter alia, the reduced amount of energy required to generate the reduced oxygen concentration airflows (e.g., MEOA airflows) that mostly, generally only, substantially only, or only are used by the POCs of the invention (e.g., in ordinary/typical operation of the POC most of the time or nearly all the time). E.g., in aspects, POCs of the invention operate for a statistically significantly greater amount of time between required battery charges, battery charge warnings, etc., comparatively than conventional POCs (e.g., when studied in an adequately powered study of the inventive POCs compared to such conventional POCs being operated under similar/identical conditions except with respect to the volume and concentration of enriched oxygen mostly, generally only, or only being delivered by the inventive POCs in such a study (or such studies).

In aspects, the POC is equipped with equipment to facilitate transport. In aspects, the POC is small enough to fit within a backpack or even a small backpack, such as a "newsboy" backpack (sling-style pack).

In aspects, the POC of the present invention is characterized by the lack of one or more components, operating parameters, or a combination thereof, which are included in the prior art patent documents and other references cited and incorporated herein by reference.

The POC typically comprises a processor, memory, pre-programmed instructions, and one or more digital displays, alarm units, and either comprises sensors or is adapted to operate with connected sensors or associated sensors. The processor typically is rated for at least 2 years of continuous use, such as about 20,000 hours of continuous use (e.g., through product testing). The processor typically comprises Bluetooth compatibility with other devices or interfaces, e.g., a mobile device application, other sensor(s), or both, or a similar local communication protocol/method. In aspects, the device is connected to the internet via a secure internet of medical things protocol that protects patient confidentiality, as are known in the art. In aspects, such communication means allow the device to also send alarms or updates to other persons monitoring performance of the device and patient, such as family members, health care providers ("HCPs"), or both.

Modes and Mode Switching

In aspects, a system of the invention is configured to automatically change between two or more different modes upon user selection, the presence of a condition (e.g., detected by a sensor and relayed to a programmable controller), or both. E.g., in aspects, a system such as a POC is capable of switching from continuous delivery and pulse delivery based on feedback from one or more sensors, e.g., a sensor associated with the oxygen delivery interface (e.g., a sensor regarding the timing, volume, or other aspects of breathing of the patient), such as when the patient's breathing meets or exceeds one or more parameters, such as when the patient's breathing meets or exceeds one or more pre-programmed breathing rate(s), volume(s), or similar threshold(s) (e.g., blood oxygen concentration).

"Continuous delivery" of oxygen is understood in the art to mean a substantially uninterrupted flow of oxygen to the patient, usually, mostly, generally, substantially, or only at a set volume of airflow (e.g., a rate measured in liters per minute). Continuous delivery mode(s) can be employed to deliver MEOA(s), IEOA(s), HEOA(s), or a combination thereof. In one aspect, continuous delivery at least sometimes, mostly, generally, substantially, or only comprises delivery of HEOA/IEOA, typically delivery of an IEOA. In aspects, most patients, generally all patients, or substantially all patients receive pulse delivery most of the time, generally all the time, or substantially all the time during treatment. True continuous flow modes are, accordingly, typically not intermittent. However, intermittent continuous flow methods also can be used in methods/systems of the invention, as discussed below.

In aspects, continuous delivery is applied, e.g., while the patient is sitting still or sleeping, e.g., as determined by one or more factors (breathing rate, movement, etc.), timers, or combinations thereof. E.g., continuous delivery can be performed when there is a detection of such conditions in a recipient/patient. For example, where heart rate, breathing rate, motion, or a combination thereof point to such conditions being present. In aspects, continuous delivery is triggered in low oxygen conditions. In aspects, low oxygen conditions that may present a significant risk of injury or death trigger continuous flow of high concentration oxygen at high flow rates (e.g., ≥4, 5, 6, or 7 LPM, at a concentration of ≥90%, ≥93%, ≥95%, or ≥97%).

A POC can deliver any suitable volume of enriched oxygen airflow in continuous delivery. The volume will depend on the mode of operation of the POC, as continuous delivery can be performed using MEOA, or HEOA/IEOA, or both.

In one exemplary aspect, a POC is configured to deliver about 240-1200 mL, such as about 240-1080 mL, ~240-960 mL, ~240-720 mL, or ~240-640 mL of an EOA, per average respiration period (e.g., per every 3-6 seconds), such as 290-590 mL, such as 340-540 mL, or such as 390-490 mL of an EOA. In aspects, a POC is configured in continuous flow mode(s) to deliver ~250-1,000 mL of EOA, such as HEOA or IEOA to a patient per average respiration or deliver EOA at a rate of 5-10 LPM. In aspects, most of the time, generally all the time, substantially all the time, or all the time continuous flow mode(s) are employed the airflow delivered to the patient is HEOA or IEOA, and typically an IEOA (e.g., an IEOA at a volume of at least ~3 LPM or ~5 LPM, such as ≥~5 LPM, e.g., 2.5-10 LPM, 4-10 LPM, 5-10 LPM, 5-8.5 LPM, or 5-7.5 LPM). In aspects where MEOA is delivered continuously, flow rates can be at least about 7.5 LPM, such as at least about 8, 8.5, 9, or at least about 9.5 LPM (e.g., 8-10 LPM, 8-12 LPM, 7.5-12.5 LPM, or 9-12 LPM). In aspects, continuous flow mode(s) do not deliver MEOA. In aspects, continuous flow mode(s) comprise MEOA delivery.

In aspects, the patient occasionally has or is at risk of having an oxygen demand equivalent to delivery of 5 LPM IEOA or greater (e.g., 4 LPM HEOA), and the method comprises triggers that cause a switch to continuous flow mode(s) at least a significant amount of time per treatment regimen, calendar quarter, or year (e.g., at least 5% of the time, or at least 10%, at least 15%, at least 20%, at least 25%, or at least 33% of days). In aspects, the patient has been diagnosed or self-diagnosed as being a "mouth breather," e.g., during sleep or other periods, and the method comprises application of continuous flow at least an appreciable or material amount of time during any such period. In aspects, the patient has sleep apnea or another disease/condition that requires use of a CPAP or BiPAP device and the method comprises application of continuous flow when such device(s) also are employed to treat the condition.

"Pulse delivery" of oxygen provides "puffs" or discrete "doses" of enriched oxygen with each patient inhalation, per a set time, or both. In aspects, a pulse delivery mode solely uses one or more forms of pulse delivery. In other aspects, pulse delivery modes use intermittent continuous flow methods. In still other aspects, pulse delivery modes use a hybrid of true pulse delivery and intermittent continuous flow delivery. In one aspect, a pulse delivery mode comprises a rest period between inhalations where no enriched oxygen airflow is released to the patient. In aspects, methods/systems of the invention ("methods/systems") are characterized in that ≥50%, ≥65%, ≥75%, ≥80%, ≥85%, or ≥90% of the air intake on average of a recipient/patient is oxygen generated by the POC, as opposed to ordinary atmospheric air.

In one pulse delivery mode a fixed amount of oxygen is delivered each time an operationally linked sensor or set of sensors detects inhalation, and then stops until the person takes another breath (such modes are used in POCs comprising "oxygen conserver" systems). In aspects, pulse delivery mode(s) comprise demand delivery, where continuous EOA flow is delivered until the system detects that a user has exhaled (dual lumen technology uses such a delivery system). In aspects, pulse delivery mode(s) comprise hybrid delivery, where EOA is delivered as a pulse at the beginning, and the system then employs a lower or declining continuous flow delivery until the user exhales (as is used in pneumatic conserver systems). In still another aspect, pulse delivery mode(s) comprise minute volume delivery, in which a fixed amount of EOA per minute is delivered, but with the volume depending on the breathing rate of the user (slower breathing rate being associated with larger amount of oxygen per breath; faster breathing rate associated with a smaller amount of oxygen per breath). In aspects, pulse delivery mode(s) comprise uniform pulse delivery, where the same volume of EOA is delivered with every breath, regardless of the breathing rate (slower breathing rate equals less oxygen delivery over the course of a minute; faster breathing rate equals more oxygen delivery over the course of a minute). Pulse delivery mode(s) typically do not comprise providing enriched oxygen airflow at a set level per minute like continuous delivery over sustained periods (e.g., longer than a patient breath, or more than 2, 3, or 4 patient breaths). In aspects, pulse delivery comprises more than one pulse delivery mode, each pulse delivery mode comprising different oxygen concentrations, different volumes of enriched oxygen airflow, or both. Pulse delivery accordingly promotes energy efficiency and a longer battery life. The ability to perform pulse oxygen delivery also distinguishes some POCs from other oxygen delivery systems that only operate in continuous delivery mode.

In aspects, methods of the invention or settings of systems comprise two or more pre-programmed pulse delivery settings (e.g., 3, 4, or 5 pulse delivery settings). In aspects, one or more of the pre-programmed pulse delivery settings delivers the volume of EOA, concentration of oxygen in the EOA, or both, in response to one or more parameters, such as decreases in breathing rate (indicating, e.g., the subject is sleeping). In aspects, patients sleeping may receive such an "enhanced bolus" pulse delivery, continuous delivery, or both, e.g., during periods of lower/low normal oxygen/air intake, such as during sleep, or during periods in which breathing becomes shallow/difficult or less frequent. In aspects, such enriched airflow conditions are also applied when other low oxygen intake conditions are detected in a subject. In aspects, a controller is preprogrammed to respond to, e.g., ≥1, ≥2, or ≥3 conditions (e.g., low oxygen in the patient, high breath demand, low volume produced by POC, high concentration oxygen produced by the POC, or a combination thereof). In aspects, a controller (computer processor and instructions of a system) is adapted to also or alternatively apply ≥2, ≥3, ≥4, or ≥5 different combinations of volume, flow, and oxygen concentration in response to those conditions, based on user selection, based on other preprogrammed factors (e.g., time), or any combination thereof.

In aspects, the system or method is configured to deliver most, generally all, substantially all, or all the EOA within a set period, such as within about 500 milliseconds, about 400 milliseconds, or about 300 milliseconds of detection of inspiration, when in pulse delivery. In aspects, however, an appreciable amount, material amount, at least about 25%, at least about 33.33%, or most of the EOA delivered is delivered after about 400 milliseconds from detection of inspiration, such as in cases wherein assuring a higher volume of EOA is desired. The response time in detection of breathing is typically at least as good (e.g., at least as sensitive) as in the Inogen One® series POCs delivering HEOA and typically uses the same or similar methods of detecting breathing rate.

A POC can deliver any suitable volume of oxygen in pulse mode(s). In aspects, the volume of EOA(s) delivered in a system/method is greater than that typically delivered in present commercial POCs, such as Inogen One® G Series POCs (e.g., a significant increase or an increase of at least about 10%, at least about 20%, at least about 25%, at least about 33%, at least about 40%, at least about 50%, at least about 66.66%, at least about 75%, at least about 90%, or at least about 100% (2x), such as at least about 50-125%, 65-115%, 70-110%, 80-110%, or 85-105% of the average or typical pulse delivery of Inogen One® POC systems.

A POC can deliver any suitable volume of EOA of any suitable oxygen concentration. Typically, an appreciable amount, a material amount, or more, such as at least about 25%, at least about 33.33%, or most of the EOA delivered in pulse delivery mode(s) of a method/system comprises MEOA. In aspects, a POC is configured to perform pulse delivery of about 80-600 mL of an MEOA to the patient per inspiration in one or more mode(s), such as 280-540 mL, such as 300-520 mL, such as 320-500 mL, such as 340-480 mL, such as 360-460 mL, such as 380-440 mL, such as 400-420 mL of an MEOA per inspiration.

Efficient and Effective MEOA

In further aspects, methods/systems are configured to generate an MEOA comprising an oxygen concentration of between about 30-49%, such as between about 30-35%, such as between about 37-42%, or such as between 39-49% and pulse delivering an effective amount, such as a therapeutically effective amount, of MEOA to the patient. An "effective amount" typically means an amount that is capable of significantly increasing oxygen in the patient. A "therapeutically effective amount" means an amount effective to treat or prevent the low oxygen condition, disease, or risk associated with low oxygen conditions. In aspects, the amount of oxygen is an IEOA equivalent amount. Such an equivalent amount means an amount wherein the amount of oxygen delivered (e.g., in mmol oxygen) is about the same as, statistically not different from, clinically not different from (e.g., based on significant results in clinical or non-clinical tests) as application of IEOA under typical pulse conditions used in the market (e.g., about 1-5 LPM), or a combination thereof.

In aspects, an amount of enriched oxygen airflow delivered in the method or by the system comprises about 80-about 600 mL of the MEOA per inspiration, such as about 80-about 240 mL such as about 90-230 mL, such as about 100-220 mL, such as about 110-210 mL, such as about 120-200 mL, such as about 130-190 mL, such as about 140-180 mL, such as 150-170 mL, such as 280-540 ml, such as 300-520 mL, such as 320-500 mL, such as 340-480 mL, such as 360-460 mL, such as 380-440 mL, such as 400-420 mL per inspiration.

In aspects, MEOA(s) is/are delivered to the patient over a period of at least 1 month, such as at least one calendar quarter, at least 4 months, at least 6 months, or at least one year. In aspects, the methods/systems comprise testing the patient for tolerance of moderately enriched oxygen airflow under supervision of a healthcare provider before allowing the patient to self-manage the portable oxygen concentrator.

In aspects, when the MEOA is pulse administered, the present methods/systems can deliver a statistically similar amount of millimoles of oxygen per inspiration of MEOA as the average typically delivered average millimoles of oxygen in pulse administration of a typical volume of an HEOA or IEOA delivered to a patient using conventional POCs. In aspects, the amount of oxygen delivered to the patient per inspiration of MEOA is about the same as the amount of millimoles of oxygen delivered to the patient per inspiration from an HEOA concentrator having an oxygen concentration of at least about 90%.

In further aspects, the methods/systems are configured to administer between about 0.05 mmol to about 0.5 mmol of oxygen such as between about 0.08 to about 0.45, such as between about 0.1 to about 0.4, such as between ~0.15 to ~0.35 mmol, or such as between about 0.2 to about 0.3 mmol of oxygen to the patient. In yet another aspect, methods/systems are configured to administer approximately the same mmol of oxygen as administered by currently available HEOA systems such as an Inogen One® G POC.

Select System Components

Systems of the invention can comprise any suitable components found in POCs in the art. The features of select components are described briefly here.

Sensors

The methods/systems of the present invention utilize one or more sensor(s) configured to detect changes in or associated with a patient, the device, or both. In an aspect, sensor(s) detect one or more aspects of patient oxygen intake (e.g., oxygen concentration). In an aspect, the one or more sensors comprise breath/breathing rate sensors. Breath/breathing rate sensors monitor a user's breathing patterns and communicate with the system such that the user receives oxygen at a level correlated with the breath/breathing rate. In an aspect, the one or more breath/breathing rate sensors are configured to monitor breathing of the patient through the oxygen delivery interface and relay information to the controller such that the controller can determine whether one or more aspects of a user's breathing exceeds one or more pre-programmed thresholds. Such sensor(s) are known in the art and described/referenced in incorporated references.

In aspects, sensor(s) detect one or more features of the user's breathing that result in a change in airflow from an MEOA to an IEOA. In another aspect, the one or more breath/breathing rate sensors detect one or more features of the user's breathing that result in a change in airflow from an IEOA to an MEOA (examples of such sensors are described in U.S. Pat. No. 10,859,456). In yet another aspect, the one or more breath/breathing rate sensors detect one or more features of the user's breathing that result in a change in oxygen delivery from a pulse delivery to a continuous delivery or from a continuous delivery to a pulse delivery based on whether the breathing of the patient exceeds the one or more pre-programmed thresholds.

In further aspects, the system can comprise one or more physiological sensors that can measure one or more levels associated with the patient such as heart rate, pulse, body temperature, skin temperature, etc.

Nitrogen Adsorption Media

In general, the methods/systems of the invention can be practiced with any suitable method for enriching oxygen from air or simply while delivering an oxygen airflow comprising an oxygen concentration that is enriched with respect to atmospheric oxygen concentrations. One commonly employed method for obtaining EOAs is the use of NAMs.

In an aspect, the system comprises a nitrogen adsorption media system, such as a rapid swing nitrogen adsorption media system or any other suitable nitrogen adsorption system used in the art, such as the system used in Inogen® POCs which are configured to deliver HEOA. Any suitable type of nitrogen adsorption system can be used. Such systems and related principles/technology are described in, e.g., U.S. Pat. No. 7,763,103, GB955894, U.S. Pat. Nos. 4,971,609, 6,691,702, JP 2010-227517, U.S. Pat. No. 3,533, 221, EP1401557, US 2012/0266883, U.S. Pat. No. 8,894, 751, and WO2015015852. In aspects, the POC comprises a system that monitors the NAM and notifies the user when replacement or maintenance is required/beneficial.

NAMs are known in the art and generally any suitable NAM can be used in the systems/methods of the invention. Briefly, nitrogen adsorption media is configured to remove nitrogen from the ambient air when it is exposed to the ambient air and acted on by a pressurized air flow that is sent through the media. The pressurized airflow traps the nitrogen molecules found in the ambient air, while the remaining oxygen flows through, creating an enriched oxygen airflow. The nitrogen adsorption media can be comprised of one or more of any type of nitrogen adsorption media known in the art including zeolite minerals, such as zeolite 5A and zeolite13X, single-wall carbon nanotubes ("SWNTs"), and double-wall carbon nanotubes ("DWNTs").

It is understood that molecular sieve beds used to separate the oxygen from the nitrogen in pressure swing adsorption or vacuum pressure swing adsorption cycles are subject to corruption by water. The water molecule strongly binds to the cation that causes selectivity in the zeolite crystal. Under normal operating conditions, this water cannot be removed, and as a result, the purity of the product gas produced by the system is reduced. Said reduction in purity, at a constant volume, reduces the therapeutic value of such portable oxygen concentrators.

In aspects, as the current POC is configured to operate at lower oxygen concentrations such as LMEOA and HMEOA, the molecular sieve beds of the present POC are configured to hold a greater amount of water molecules as compared to known POCs that administer oxygen at approximately 90%. In an aspect, the sieve beds of the present invention can hold at least an amount of water molecules that is at least statistically significantly more as compared to known POCs. In aspects the current POC can hold at least 10% more water molecules, such as at least 20% more water molecules, such as at least 30% more molecules, such as at least 40% more water molecules, such as at least 50% more water molecules, such as at least 60% more water molecules, such as at least 70% more water molecules, such as at least 80% more water molecules, such as at least 90% more water molecules, such as at least 100% more water molecules, or such as more than 100% more water molecules as compared to known POCs. In aspects, systems/POCs of the invention operate on average with a significantly higher amount of water vapor present in the EOA delivered by the POC (e.g., in MEOA, such as LMEOA) as compared to a HEOA POC, such as an Inogen One POC. E.g., the amount of water vapor in aspects in an average pulse of MEOA delivered by an inventive system/POC is $\geq 5\%$, $\geq 10\%$, $\geq 15\%$, or $\geq \sim 20\%$ that of the average water vapor in an HEOA POC.

In aspects, the controller of the present POC can sense the purity of oxygen being delivered and can administer an increased volume of delivered gas at a decreased purity in order to maintain the same therapeutic value as commercial units that function at the higher 90% oxygen level.

Pressure Gradient Generating System

In an aspect, the system comprises a PGGS, which is a component of a NAM "system," and that is configured to provide a pressure gradient that is selectively isolated from the environment by at least one air enrichment area separator (e.g., through the use of a compressor). In an aspect, application of the pressure gradient to the nitrogen adsorption media causes release of an enriched oxygen airflow.

The air enrichment area separator can be any type of barrier or enclosure known in the art, such as one or more cylinders, tubes, or canisters, that are configured to isolate the pressure gradient from the outside environment.

The pressure needed in some systems of the invention is significantly less than in current on-market systems, given the fact that lower oxygen concentrations can be used at least sometimes in operation (in an MEOA mode). In an aspect, the PGGS provides a pressure gradient in an amount of between about 10-30 PSI, such as 12-28 PSI, or such as 15-25 PSI to the nitrogen adsorption media. In aspects, the PGGS is set to sometimes, most of the time, generally always, or at least substantially always apply a pressure to a NAM that is at least about 15% less, at least about 25% less, at least about 33% less, or at least about 40% less than the pressure applied to an NAM in a conventional POC. In aspects, a POC may operate using a blower versus a compressor, at least some of the operating time, if not most of the time, generally all of the time, or at least substantially all of the time. In aspects, a compressor component of a POC is operated at a reduction in time, intensity, energy expenditure, speed, or any combination thereof in a system/method of the invention as compared to conventional POC systems (e.g., by a reduction of at least 10%, $\geq 15\%$, $\geq 20\%$, $\geq 25\%$, or $\geq \sim 33\%$ in one, some, most, or all of such characteristics).

Patient Oxygen Delivery Interface

In a further aspect, the system comprises a PODI that is configured to administer the enriched oxygen to the patient. In an aspect, the breathing of the patient is monitored through the PODI to determine whether to switch between continuous delivery and pulse delivery of the oxygen and/or to determine the timing of one or more EOA dose administrations. The PODI can be any type of PODI known in the art such as a nasal cannula, a simple face mask, a partial rebreather face mask, a non-rebreather face mask, or a tracheostomy mask. In aspects, a system can be used with both a nasal cannula and mask PODI. In methods, most, generally all, or substantially all the time the patient receives EOA delivery through a nasal cannula. In an aspect the PODI is configured to fluidly connect to a flow line which is further configured to connect to an airflow outlet on the system. Such systems are known in the art.

Controller

In an aspect, the system comprises a programmable controller component, which further comprises stored computer-readable instructions (memory) and a processor component configured to read and execute the computer-readable instructions.

The controller typically is composed of machine-readable instructions encoded in physical, transferable, and reproducible or at least non-transient computer readable media and suitable computer processors. The controller of the POC can typically be considered a specialized computing device, in the sense that most, generally all, substantially all, or all of its encoding is configured for the control of the operation of the other components of the POC, such as the operation of the pressure gradient generating system, the delivery of the volume of oxygen to the patient, interfacing with sensor(s), relaying of display information in the POC or an associated specialized interface (such as a mobile phone application, web page, or both), triggering of POC alarm(s), and the like. The instruction component of the controller is typically programmable by a suitable programming language. Software/hardware systems are commonly used in modern POCs, such as Inogen® POCs, and examples of such systems have been described in the art (see, e.g., WO2020037375, WO2011127314, WO2019202390, U.S. Pat. Nos. 6,651,658, and 9,717,876).

In an aspect, the controller is configured to determine whether one or more aspects of the patient's breathing exceeds one or more thresholds. In an aspect, the controller is configured to control the volume of the airflow delivered to the patient and the oxygen concentration of the airflow delivered to the patient. In a further aspect, if the controller determines that the one or more aspects has exceeded the one or more thresholds, the controller is further configured to cause the system to automatically change between continuous and pulse delivery of oxygen through the PODI. In aspects, the invention comprises modifying the controller in such a manner so as to configure the POC to generate and deliver the EOA as described herein. Such modification(s) can, in aspects, be performed by the original POC manufacturer prior to sale of the POC. In aspects, such modification(s) can be made programmatically, e.g., through the modification of operational code, e.g., proprietary code, of the POC.

In an aspect, the PODI is configured to stay open for a statistically significantly greater period of time than currently available HEOA systems such as an Inogen One® G POC when in pulse delivery. In a further aspect, the PODI can stay open for any period of time which results in a longer administration period during the pulse, such as 50 milliseconds longer, such as 100 milliseconds longer, such as 200 milliseconds longer, such as 300 milliseconds longer, such as 400 milliseconds longer, etc.

In an aspect, the controller is configured to determine whether one or more physiological sensors exceeds one or more thresholds. In further aspects, the controller is configured to trigger an alarm component when the pulse-delivered oxygen changes to continuously delivered oxygen. The alarm can be any type of alarm known in the art, including a beep, siren, buzz, or other sound. In further aspects, the alarm can link with an app such as on a mobile phone in order to connect with additional individuals such as a caretaker, nurse, physician, facility manager, family member, etc.

ILLUSTRATIVE EMBODIMENTS SHOWN IN THE FIGURES

FIG. 1 is an abstract representation of the application of principles underlying the methods and devices of the present invention. FIG. 1 shows two containers with varying volumes of air, representative of a unit volume of air delivered by a POC. The larger container on the left (100) is representative of the features of a unit volume of air provided by the present invention. The smaller container on the right (110) is representative of the features of a unit volume of air provided by a POC of the prior art (delivering at least 80% enriched oxygen). As shown by the dotted line (unlabeled) within the first container (100), the unit volume of air of the second, smaller container (110) is approximately half the size of the unit volume of air provided by the larger container. Diameter (140) further illustrates the equal diameters of each of the two representative unit volume containers. Containers (100) and (110) demonstrate the molar ratio of oxygen molecules within the two systems. The first container (100) illustrates the present invention providing oxygen in an amount of 4 molecules of enriched oxygen (120) per every 6 molecules of non-enriched or ambient air molecules (130), or a 40% moderately enriched oxygen concentration, while the second container (110) illustrates commercial systems as providing 8 molecules of enriched oxygen (130) per every 2 molecules of non-enriched or ambient air molecules (120), or a highly enriched 80% oxygen concentration. One can appreciate that a similar representation could be made illustrating a commercial system providing a more typical highly enriched (90%) oxygen concentration. The 80% enrichment was simply chosen for ease of presentation in this simple drawing. The unit volumes illustrated by FIG. 1 could be any unit volume. In other words, FIG. 1 is a simple figure used to aid in the understanding of the basic concepts underlying the lower concentration oxygen system(s) and device(s) provided by the invention.

Figure 2:
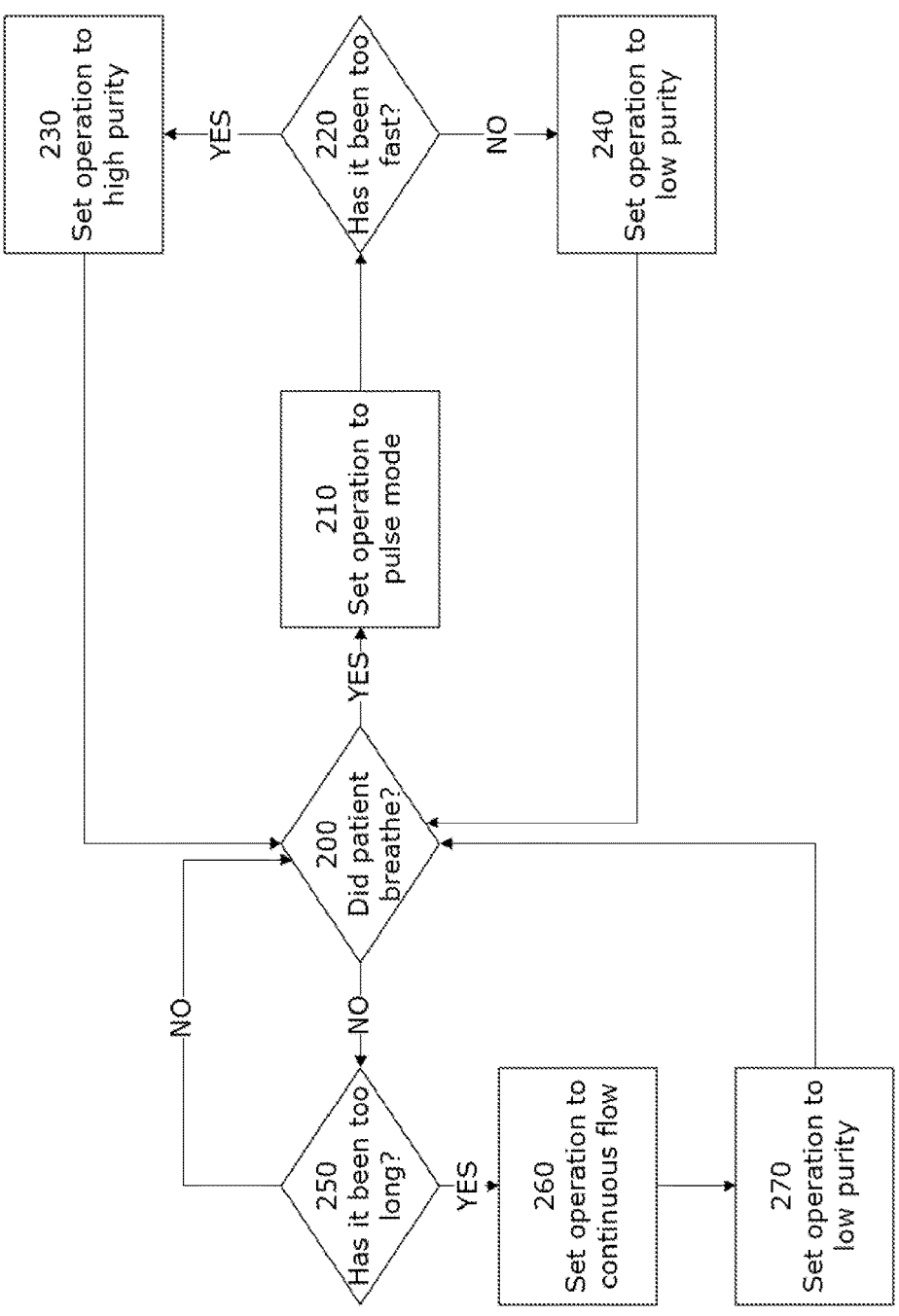
FIG. 2 is a flow chart representing the steps of operation of a portable oxygen concentrator according to aspects of the present invention.

FIG. 2 is a flow chart representing a process of using a portable oxygen concentrator according to aspects of the invention. Initially, an analysis is performed to determine whether a patient has taken a breath (200). If the patient has taken a breath, the operation of the portable oxygen concentrator is set to pulse mode (210). Once in pulse mode, an analysis is performed to assess whether the pulse is being administered too quickly (220). If the pulse is being administered too quickly, the operation is set to high purity (230). The process is then repeated to determine whether the patient has taken a breath (200). If so, the operation is again set to pulse mode (210). If upon analysis (220) it is determined that the pulse is not being administered too quickly, the operation is set to low purity (240). The process is then repeated to determine whether the patient has taken a breath (200). If upon analysis (200) it is determined that the patient has not taken a breath (no breathing is detected), an analysis is performed to determine whether the time between two breaths has passed a pre-established threshold (250). If the pre-established threshold has been surpassed, the operation of the portable oxygen concentrator is set to continuous flow (260). Once in continuous flow, operation is set to deliver high purity oxygen (270). The process is then repeated to determine whether the patient has taken a breath (200). If upon analysis it is determined that the pre-established threshold for time between two breaths has not been surpassed (250), the system again determines whether breathing is detected (200), and the full process described here is repeated.

Figure 3:
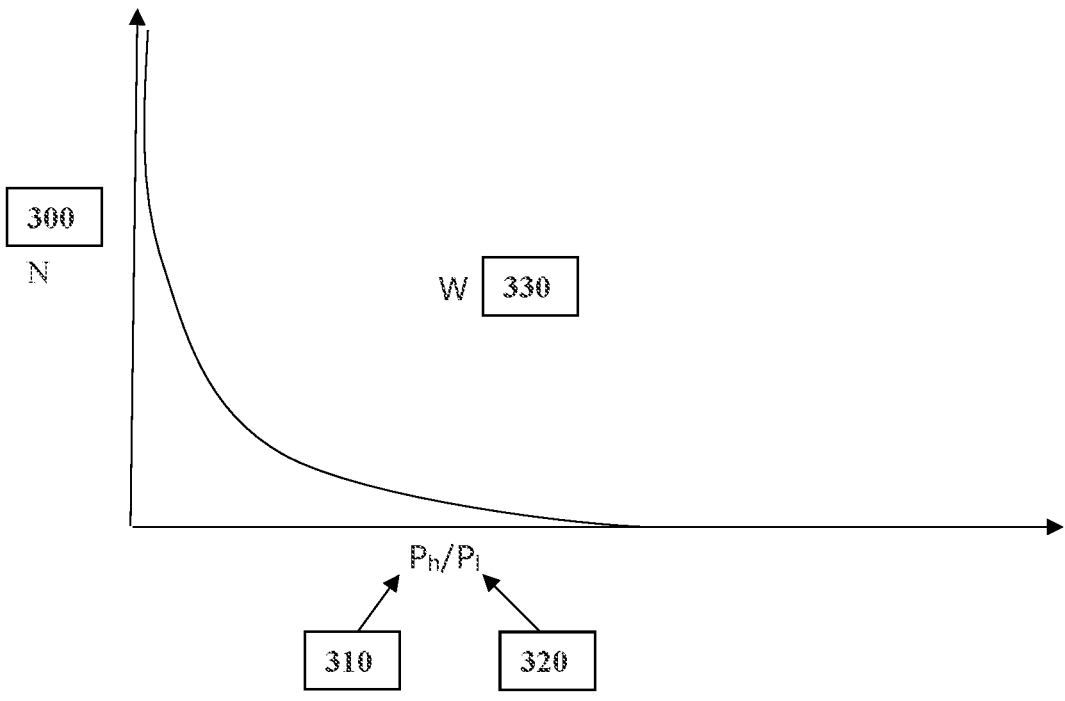
FIG. 3 is a graph demonstrating the number of moles of gas (n), e.g., oxygen gas, that can be moved by a compressor at various operating pressure ratios (PH/PL), where the work (W) is kept constant.

FIG. 3 is a graph demonstrating the number of moles of gas (300), e.g., oxygen gas, that can be moved by a compressor at various operating pressure ratios, the pressure ratio represented by pressure high (310) divided by pressure low (320) (PH/PL), where the work (330) is kept constant.

Figure 4:
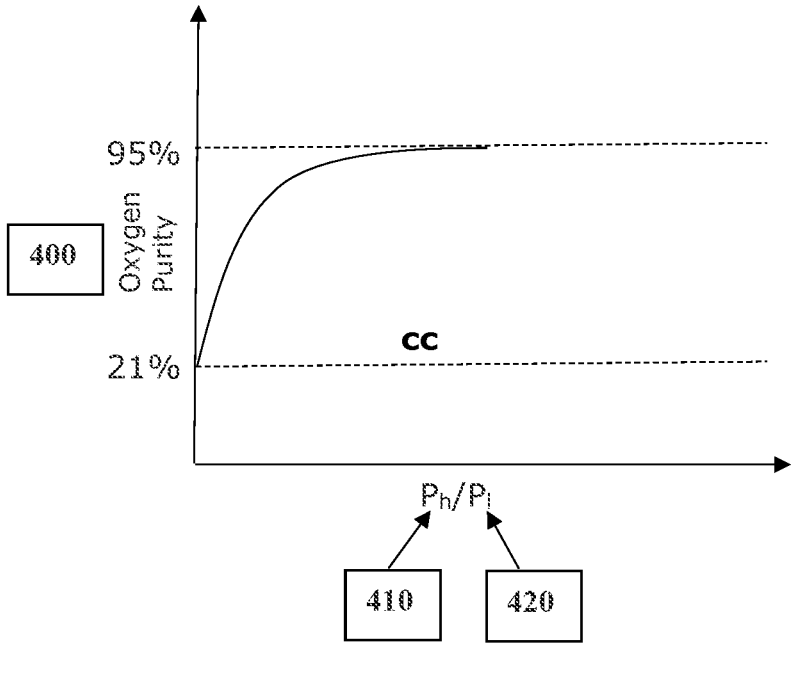
FIG. 4 is a graph demonstrating the oxygen purity that can be produced at various operating pressure ratios (PH/PL).

FIG. 4 is a graph demonstrating the oxygen purity (400) that can be produced at various operating pressure ratios, the pressure ratio represented by pressure high (410) divided by pressure low (420) (PH/PL).

FIG. 5 is a flowchart illustrating exemplary steps of operation of a system/POC or steps of a method of the invention comprising 1 or 2 possible alarms that are triggered by certain possible operating conditions. The flowchart begins in block 501 where the operation of the device begins under MEOA (not shown), e.g., LMEOA generating conditions. Next, the oxygen concentration is detected in the POC output 505. Next it is determined whether the oxygen level is above the target maximum oxygen concentration (e.g., 40-50%, 45-49%, 40-45%, or 40-60%), 507. If the oxygen level is not above the target maximum oxygen concentration 509, the system/method also or alternatively determines whether the airflow is below the target minimum pulse volume (e.g., below 400, 350, 300, 275, or 250 mL (or ml)/pulse) 520. If the oxygen level is above the target maximum (e.g., 40-50%, 45-49%, 40-45%, or 40-60%) 508, then the high oxygen indicator/alarm or instructions is sent to user and/or associated persons/systems (e.g., a system controller) is sent 510. If at 520 the airflow is below the target minimum (e.g., below 400, 350, 300, 275, or 250 mL/pulse) 525 then the low airflow rate alarm/indicator or instructions is sent to user and/or associated person/systems (e.g., controller) 529. If at 520 the airflow is not below the target minimum (e.g., below 400, 350, 300, 275, or 250 mL/pulse) 530, then the routine loops back to step 501.

EXEMPLARY ASPECTS OF THE INVENTION

The following is a non-limiting list of aspects of the invention.

In one aspect the invention provides a method of assisting breathing in a chronic obstructive pulmonary disease patient having low blood oxygen saturation, the method comprising (a) providing the chronic obstructive pulmonary disease patient with a portable oxygen concentrator that delivers an enriched oxygen airflow, and which comprises: (1) a pressure gradient generating system, (2) at least one nitrogen adsorption media that generates an enriched oxygen airflow when exposed to air and acted on by a sufficient pressure gradient and that is selectively isolated from the environment by at least one air enrichment area separator, (3) an enriched oxygen airflow outlet that is fluidly connected to a flow line and a patient oxygen delivery interface (such as a nasal cannula), (4) a programmable controller comprising stored computer readable instructions and a processor for executing such instructions and that in operation determines (I) the volume of the airflow delivered to the patient, (II) the oxygen concentration of the airflow, and (III) whether to deliver enriched oxygen airflow to a patient either via continuous delivery or pulse delivery, (5) one or more sensors configured to detect changes in patient oxygen intake, such as at least one breath/breathing rate sensor, and (6) an alarm component that is triggered when the oxygen concentration changes from MEOA to HEOA/IEOA oxygen, when the volume of airflow delivered to the recipient falls below a minimum target level, or both (an alarm being capable of being audio, visual, sensory, applied at the device, applied through communication devices (phones, smartphones, etc.), and optionally also or alternatively leading to transmission of instructions to control the operation of the POC/system (e.g., by increasing the time a valve is open to deliver EOA, increasing intensity of components producing oxygen or airflow, etc.). In aspects, moderately enriched airflows can be high moderately enriched airflows or low moderately enriched airflows. The alarm can be any type of alarm known in the art, including a beep, siren, buzz, or other sound. In aspects the alarm can link with an app such as on a mobile phone in order to connect with additional individuals such as a caretaker, nurse, physician, facility manager, family member, etc. (b) delivering an enriched oxygen airflow to the patient for a period of at least about 1 month, the delivery of the enriched oxygen airflow comprising (I) generating an MEOA comprising an oxygen concentration of less than 50%, such as about 30-49%, e.g., an LMEOA comprising about 30-39%, such as about 31-38%, such as about 32-37%, such as about 33-36%, or such as about 34-35%, or an HMEOA comprising about 40-49%, such as about 41-48%, such as about 42-47%, such as about 43-46%, or such as about 44-45% and (II) pulse delivering the MEOA to the patient, in an effective amount per pulse (or per average pulse or generally all pulses) (e.g., about 80-about 600 mL of a MEOA per inspiration, such as about 80-about 240 mL such as about 90-230 mL, such as about 100-220 mL, such as about 110-210 mL, such as about 120-200 mL, such as about 130-190 mL, such as about 140-180 mL, such as 150-170 mL, such as 280-540 mL, such as 300-520 mL, such as 320-500 mL, such as 340-480 mL, such as 360-460 mL, such as 380-440 mL, such as 400-420 mL, such that the average millimoles of oxygen delivered to the patient per inspiration is statistically similar to the amount of millimoles of oxygen delivered to the patient per inspiration of a highly enriched oxygen airflow having an oxygen concentration of about 90%, (c) monitoring breathing of the patient through the patient oxygen delivery interface, and (d) automatically changing between continuous delivery and pulse delivery based on the timing of the detection of breathing of the patient through the patient oxygen delivery interface when the controller determines that one or more aspects of the patient's breathing exceeds pre-programmed threshold(s) (aspect 1).

In one aspect, the invention provides the method of aspect 1, wherein in continuous delivery the portable oxygen concentrator delivers about 240-640 mL of either an intensively enriched oxygen airflow or highly enriched oxygen airflow (aspect 2).

In one aspect, the invention provides the method of aspect 1 or aspect 2, wherein the portable oxygen concentrator switches from pulse delivery to continuous delivery or vice versa at least once per day (e.g., 24-hour interval) on average during the at least 1-month period (aspect 3).

In one aspect, the invention provides the method of any one of aspects 1-3, wherein the method further comprises automatically changing the oxygen content of the portable oxygen concentrator's airflow from a low moderately enriched oxygen airflow or a high moderately enriched airflow to an intensively enriched oxygen airflow or highly enriched oxygen airflow based on the detection of one of more conditions (aspect 4).

In one aspect, the invention provides the method of any one of aspects 1-4, wherein the method further comprises automatically changing the airflow from an intensively enriched oxygen airflow or highly enriched oxygen airflow to a low moderately enriched oxygen airflow or a high moderately enriched airflow based on the detection of one or more conditions comprising one or more breath/breathing rate conditions in the patient (aspect 5).

In one aspect, the invention provides the method of any one of aspects 1-5, wherein the average rate of enriched airflow to the patient in continuous delivery, pulse delivery, or both, is at least about 3.3 L/minute (aspect 6).

In one aspect, the invention provides the method of aspect 6, wherein the average rate of enriched airflow to the patient in continuous delivery, pulse delivery, or both, is greater than 3.6 L/minute (aspect 7).

In one aspect, the invention provides the method of any one of aspects 1-7, wherein the average oxygen intake per inspiration of the patient is about 0.05 mmol to about 0.5 mmol oxygen (aspect 8).

In one aspect, the invention provides the method of any one of aspects 1-8, wherein the method comprises operating the pressure gradient system at least about 33% longer, opening the air enrichment area separator at least about 33% longer, or both, as compared to the default operating parameters of an HEOA system such as the Inogen One® G3, Inogen One® G4, or Inogen One® G5 POCs (aspect 9).

In another aspect, the invention provides a method wherein the nitrogen adsorption media comprises sieve beds that are configured to maintain the therapeutic level of oxygen for a period of greater than 1 year, such as greater than 18 months, such as greater than 2 years, such as greater than 3 years, such as greater than 4 years, such as greater than 5 years (aspect 10).

In one aspect, the invention provides the method of any one of aspects 1-10, wherein the method comprises applying a pressure gradient comprising a maximum pressure of between 10-30 PSI to the nitrogen adsorption media (aspect 11).

In another aspect, the invention provides a method wherein the nitrogen adsorption media comprises sieve beds that are configured to maintain the therapeutic level of oxygen for a period of greater than 1 year, such as greater than 18 months, such as greater than 2 years, such as greater than 3 years, such as greater than 4 years, such as greater than 5 years (aspect 12).

In one aspect, the invention provides the method of aspect 12, wherein the delivery of oxygen consumes an average of between about 30-90 Watts of energy, such as between about 30-60 Watts of energy (aspect 13).

In one aspect, the invention provides the method of any one of aspects 1-13, wherein the concentration of oxygen in the moderately enriched airflow is about between about 30-49% and the average volume of moderately enriched airflow delivered per inspiration is between about 80 mL to about 600 mL, such as 280 mL to about 580 mL, 300 mL to about 600 mL, 310 mL to about 650 mL, 310 mL to about 550 mL, or 290 mL to about 550 mL (aspect 14).

In one aspect, the invention provides the method of any one of aspects 1-14, wherein the average volume of moderately enriched airflow delivered per inspiration is between about 280-540 mL, about 285-525 mL, about 290-490 mL, or about 290-450 mL (aspect 15).

In one aspect, the invention provides the method of aspect 15, wherein the average volume of moderately enriched airflow delivered per inspiration thereof is at least about 300 mL (aspect 16).

In one aspect, the invention provides the method of aspect 16, wherein the average volume of moderately enriched airflow delivered per inspiration is at least about 350 mL, at least about 375 mL, at least about 400 mL, ≥450 mL, or at least ~500 mL (aspect 17).

In one aspect, the invention provides the method of any one of aspects 1-17, wherein the patient has an average blood oxygen saturation of lower than about 93% or 92%, such as about 88%-92%, at the start of the method (aspect 18).

In one aspect, the invention provides the method of any one of aspects 1-18, wherein the method comprises testing the patient for tolerance of moderately enriched oxygen airflow under supervision of a healthcare provider before allowing the patient to self-manage the portable oxygen concentrator (aspect 19).

In one aspect, the invention provides the method of any one of aspects 1-19, wherein the portable oxygen concentrator generates an average of less than 50 decibels of noise in operation (aspect 20).

In one aspect, the invention provides the method of any one of aspects 1-20, wherein the method is performed for a period of at least about 6 months (aspect 21).

In one aspect, the invention provides the method of any one of aspects 1-21, wherein the airflow to the patient consists essentially of oxygen enriched air (aspect 22).

In one aspect, the invention provides the method of any one of aspects 1-22 wherein the alarm can be triggered when the oxygen concentration exceeds the level typically associated with MEOA (aspect 23).

In one aspect, the invention provides the method of any one of aspects 1-23 wherein the alarm can be triggered when the oxygen concentration exceeds the level typically associated with either HEOA or IEOA (aspect 24).

In an aspect, the POC is equipped with a manual shut off for the alarm, such as when the patient decides to manually change the administration to continuous flow, e.g., when preparing to go to sleep (aspect 25).

In another aspect, the POC can be equipped with one or more physiological sensors associated with the patient that can be monitored, recorded, and also can be linked to predetermined threshold values. In further aspects, the sensors can measure one or more of heart rate, pulse, body temperature, skin temperature, etc. (aspect 26).

In another aspect, the controller can be programmed, upon activation of an alarm, to compare the readings of the one or more physiological sensors and compare the values to the predetermined threshold to see if the oxygen mode change is associated with a concerning value that may require sending a message to a healthcare provider or caretaker for assistance (aspect 27).

In one aspect, the invention provides a system for increasing oxygen intake in a patient requiring oxygen supplementation comprising a portable oxygen concentrator device configured to provide the patient with an enriched oxygen airflow, the portable oxygen concentrator comprising (a) a pressure gradient generating system, (b) at least one nitrogen adsorption media configured to generate an enriched oxygen airflow when exposed to air and acted on by a sufficient pressure gradient and that is selectively isolated from the environment by at least one air enrichment area separator, (c) an enriched oxygen airflow outlet that is fluidly connected to a flow line and a patient oxygen delivery interface, (d) a programmable controller comprising stored computer readable instructions and a processor to determine (1) the volume of the airflow delivered to the patient, (2) the oxygen concentration of the airflow, and (3) to cause delivery of enriched oxygen airflow to a patient either via continuous or pulse delivery, (e) one or more sensors configured to detect changes in patient oxygen intake, such as at least one breath/breathing rate sensor, and (f) and an alarm that can be configured to alert when the oxygen administered changes from MEOA to HEOA or IEOA wherein in operation (1) the controller controls the operation and operating conditions of the pressure gradient generating system, the at least one air enrichment area separator, the enriched oxygen airflow outlet, and the oxygen delivery interface, (2) the one or more sensors are configured to monitor breathing of the patient through the oxygen delivery interface and determine whether one or more aspects of a user's breathing exceeds one or more pre-programmed thresholds, (3) the controller causes the delivery of enriched oxygen to change from a pulse delivery to a continuous delivery and back again based on whether the breathing of the patient exceeds the one or more pre-programmed thresholds, and (4) in pulse delivery the system generates and delivers a moderately enriched oxygen airflow comprising between 30-49% oxygen and delivers the moderately enriched oxygen airflow in a pulse delivery comprising about 80-about 600 mL per inspiration (aspect 28).

In one aspect, the invention provides the system of aspect 28, wherein the portable oxygen concentrator is configured to deliver to the patient about 240-640 mL (e.g., 280-580 mL, 290-550 mL, 300-550 mL, 300-500 mL, 290-540 mL, 280-540 mL, or 350-450 mL) of an intensively enriched oxygen airflow or highly enriched oxygen airflow (aspect 29).

In one aspect, the invention provides the system of aspect 28 or aspect 29 wherein the portable oxygen concentrator is configured to switch from pulse delivery to continuous delivery, from continuous delivery to pulse delivery, or any combination thereof, at least once per 24-hour interval on average (aspect 30).

In one aspect, the invention provides the system of any one of aspects 28-30 wherein the portable oxygen concentrator is configured to change the airflow from the moderately enriched oxygen airflow to the intensively enriched airflow or highly enriched oxygen airflow, from the intensively enriched oxygen airflow or highly enriched oxygen airflow to the moderately enriched oxygen airflow, or any combination thereof, based on the detection of one of more system or patient conditions (aspect 31).

In one aspect, the invention provides the system of any one of aspects 28-31, wherein the average rate of enriched airflow to the patient in continuous delivery, pulse delivery, or both, is at least about 3.3 L/minute (e.g., ≥4, 4.5, 5, 5.5, 6, 6.5, 6.75, 7, or 7.25) (aspect 32).

In one aspect, the invention provides the system of aspect 32, wherein the average rate of enriched airflow to the patient in continuous delivery, pulse delivery, or both, is greater than 3.6 L/minute (e.g., ≥4, ≥4.25, ≥5.5, ≥6.75, ≥7.33, or ≥7.5 LPM) (aspect 33).

In one aspect, the invention provides the system of any one of aspects 28-33, wherein the system is configured to deliver an average volume of about 0.05 mmol to about 0.5 mmol of moderately enriched airflow per inspiration of the patient (aspect 34).

In one aspect, the invention provides the system of any one of aspects 28-34, wherein the pressure gradient applied to the nitrogen adsorption media comprises a maximum pressure of between 15-25 PSI (aspect 35).

In one aspect, the invention provides the system of any one of aspects 28-35, wherein the delivery of oxygen consumes an average of about 30-90 Watts of energy, such as 30-60 Watts of energy (aspect 36).

In one aspect, the invention provides the system of any one of aspects 28-36, wherein the system is configured to provide a moderately enriched airflow oxygen concentration of about 30-49% and to deliver an average volume of about 280 mL to about 540 mL (e.g., 290-550, 300-500, 320-520, 320-570, 400-600, 300-600, or 330-580 mL, etc.) of moderately oxygen enriched airflow per inspiration of the patient (aspect 37).

In one aspect, the invention provides the system of any one of aspects 28-37 wherein the system is configured to deliver an average volume of between about 320-500 mL of moderately oxygen enriched airflow per inspiration of the patient (aspect 38).

In one aspect, the invention provides the system of aspect 38, wherein the system is configured to deliver an average volume of at least about 350 mL of moderately oxygen enriched airflow per inspiration of the patient (aspect 39).

In one aspect, the invention provides the system of aspect 39, wherein the system is configured to deliver an average volume of at least about 400 mL of moderately enriched airflow per inspiration of the patient (aspect 40).

In one aspect, the invention provides the system of any one of aspects 28-40, wherein the operating conditions for the system comprise operating the pressure gradient system at least about 33% longer, opening the air enrichment area separator at least about 33% longer, or both, as compared to the default operating parameters of an Inogen One® G3, Inogen One® G4, or Inogen One® G5 POC (aspect 41).

In one aspect, the invention provides the method of any one of aspects 28-41 wherein the alarm can be triggered when the oxygen concentration exceeds the level typically associated with MEOA (aspect 42).

In one aspect, the invention provides the method of any one of aspects 28-42 wherein the alarm can be triggered when the oxygen concentration exceeds the level typically associated with HEOA or IEOA (aspect 43).

In an aspect, the POC is equipped with a manual shut off for the alarm, such as when the patient decides to manually change the administration to continuous flow, e.g., when preparing to go to sleep (aspect 44).

In another aspect, the POC can be equipped with one or more physiological sensors associated with the patient that can be monitored, recorded, and also can be linked to predetermined threshold values. In further aspects, the sensors can measure one or more of heartrate, pulse, body temperature, skin temperature, etc. (aspect 45).

In another aspect, the controller can be programmed, upon activation of the alarm, to compare the readings of the one or more physiological sensors and compare the values to the predetermined threshold to see if the oxygen mode change is associated with a concerning value that may require sending a message to a healthcare provider or caretaker for assistance (aspect 46).

What is claimed is:

1. A system for assisting breathing in a patient having low blood oxygen saturation, comprising:
(1) a portable oxygen concentrator configured to deliver an enriched oxygen airflow, wherein the portable oxygen concentrator comprises:
(a) a pressure gradient generating system;
(b) at least one nitrogen adsorption media that generates the enriched oxygen airflow when exposed to air and acted on by a sufficient pressure gradient and that is selectively isolated from an ambient environment by at least one air enrichment area separator;
(c) an enriched oxygen airflow outlet that is fluidly connected to a flow line and a patient oxygen delivery interface;
(d) a programmable controller comprising stored non-transitory computer readable instructions and a processor for executing the stored instructions and wherein the controller is configured to determine:
(I) a volume of the airflow delivered to the patient,
(II) an oxygen concentration of the airflow, and
(III) whether to deliver enriched oxygen airflow to the patient via continuous delivery or pulse delivery;
(e) one or more sensors configured to detect changes in patient oxygen intake, and
(f) an alarm that is configured to relay an alert when the oxygen airflow administered changes from a moderately enriched oxygen airflow to a highly enriched oxygen airflow or an intensively enriched oxygen airflow, wherein the portable oxygen concentrator is configured to:
(I) deliver the enriched oxygen airflow to the patient for a period of at least 1 month, the delivery of the enriched oxygen airflow comprising a therapeutically effective amount of moderately enriched oxygen airflow comprising an oxygen concentration of between 30-49%,
(II) monitor the breathing of the patient through the one or more sensors configured to detect changes in patient oxygen intake, and
(III) automatically switch between at least one pulse delivery mode and a continuous delivery mode wherein in the continuous delivery mode the portable oxygen concentrator is configured to automatically:
(A) generate an intensively enriched oxygen airflow comprising an oxygen concentration of at least about 60% and
(B) continuously deliver between about 640 mL and about 1200 mL of the intensively enriched oxygen airflow to the patient per average inspiration based on a timing of detection of breathing of the patient through the one or more sensors when the controller determines that one or more aspects of the patient's breathing meets or exceeds one or more pre-programmed thresholds; and wherein the portable oxygen concentrator is configured to consume an average of 30-60 Watts of energy during operation.

2. The system of claim 1, wherein the system is configured to treat chronic obstructive pulmonary disease.

3. The system of claim 1, wherein the oxygen concentration of the intensively enriched oxygen airflow is at least about 75%.

4. The system of claim 1, wherein the continuous delivery mode is configured to deliver the highly enriched oxygen airflow to the patient, wherein the highly enriched airflow comprises an oxygen concentration of at least about 90%.

5. The system of claim 1, wherein the portable oxygen concentrator is configured to detect patient inspirations and automatically deliver at least about 75% of a pulse of moderately enriched oxygen within about 500 milliseconds of the detection of an inspiration.

6. The system of claim 5, wherein the portable oxygen concentrator is configured to detect patient inspirations and automatically deliver at least about 75% of the pulse of moderately enriched oxygen within about 300 milliseconds of the detection of the inspiration.

7. The system of claim 1, wherein generating the moderately enriched oxygen airflow comprises applying the pressure gradient, wherein the pressure gradient comprises applying a maximum pressure of between 15-25 PSI to the nitrogen adsorption media.

8. The system of claim 1, wherein the one or more sensors are configured to detect patient inhalation and exhalation and the at least one pulse delivery mode is configured to deliver an initial pulse of oxygen upon detection of inhalation and thereafter delivering a declining continuous flow of the enriched oxygen airflow until the one or more sensors detects that the patient has exhaled.

9. The system of claim 1, wherein the system further comprises a manual shut off for the alarm feature that is configured to be selectively activated by the patient.

10. The system of claim 1, wherein the system is configured to administer oxygen to the patient in the at least one pulse delivery mode in an amount of between about 80 ml and about 600 ml of moderately enriched airflow per inspiration.

11. The system of claim 10, wherein the oxygen is configured to be administered to the patient in the at least one pulse delivery mode in an amount of at least 280 ml per inspiration.

12. The system of claim 11, wherein the moderately enriched airflow has an oxygen concentration of between 30% and 39%.

13. The system of claim 1, wherein the alarm is configured to relay an alert when the volume of airflow delivered by the system falls below a minimum airflow.

* * * * *